(12) United States Patent
Bashir et al.

(10) Patent No.: US 8,945,912 B2
(45) Date of Patent: Feb. 3, 2015

(54) DNA SEQUENCING AND AMPLIFICATION SYSTEMS USING NANOSCALE FIELD EFFECT SENSOR ARRAYS

(75) Inventors: Rashid Bashir, Champaign, IL (US); Ashraf Alam, West Lafayette, IN (US); Demir Akin, Palo Alto, CA (US); Oguz Hasan Elibol, Palo Alto, CA (US); Bobby Reddy, Savoy, IL (US); Donald E. Bergstrom, Lafayette, IN (US); Yi-Shao Liu, Taichung (TW)

(73) Assignee: The Board of Trustees of the University of Illinois, Urbana, IL (US)

( * ) Notice: Subject to any disclaimer, the term of this patent is extended or adjusted under 35 U.S.C. 154(b) by 269 days.

(21) Appl. No.: 13/120,710

(22) PCT Filed: Sep. 29, 2009

(86) PCT No.: PCT/US2009/058739
§ 371 (c)(1),
(2), (4) Date: Oct. 14, 2011

(87) PCT Pub. No.: WO2010/037085
PCT Pub. Date: Apr. 1, 2010

(65) Prior Publication Data
US 2012/0021918 A1 Jan. 26, 2012

Related U.S. Application Data

(60) Provisional application No. 61/101,062, filed on Sep. 29, 2008.

(51) Int. Cl.
*C12M 1/36* (2006.01)
*C12P 19/34* (2006.01)
*G01N 27/414* (2006.01)
*C40B 20/00* (2006.01)
*B82Y 15/00* (2011.01)
*B82Y 35/00* (2011.01)

(52) U.S. Cl.
CPC .............. *G01N 27/414* (2013.01); *B82Y 15/00* (2013.01); *B82Y 35/00* (2013.01)
USPC ................... 435/287.2; 435/91.2; 422/82.01; 506/20

(58) Field of Classification Search
None
See application file for complete search history.

(56) References Cited

U.S. PATENT DOCUMENTS 2,656,508 A 10/1953 Coulter
3,999,122 A 12/1976 Winstel et al.
(Continued)

FOREIGN PATENT DOCUMENTS

EP 1 225 234 11/2007
EP 2 017 613 1/2009
(Continued)

OTHER PUBLICATIONS

Gerlach et al. (2006), "Introduction to Microsystem Technology: A Guide for Students", Carl Hanser Munich/FRG, pp. 27-29.
(Continued)

*Primary Examiner* — Betty Forman
(74) *Attorney, Agent, or Firm* — Lathrop & Gage LLP

(57) ABSTRACT

In one aspect, described herein are field effect chemical sensor devices useful for chemical and/or biochemical sensing. Also provided herein are methods for single molecule detection. In another aspect, described herein are methods useful for amplification of target molecules by PCR.

80 Claims, 13 Drawing Sheets

(56) References Cited

U.S. PATENT DOCUMENTS

| | | | |
|---|---|---|---|
| 5,430,347 A | 7/1995 | Kane et al. | |
| 5,795,782 A | 8/1998 | Church et al. | |
| 6,015,714 A | 1/2000 | Baldarelli et al. | |
| 6,017,696 A * | 1/2000 | Heller | 435/6.11 |
| 6,203,683 B1 | 3/2001 | Austin et al. | |
| 6,265,758 B1 | 7/2001 | Takahashi | |
| 6,267,872 B1 | 7/2001 | Akeson et al. | |
| 6,325,904 B1 | 12/2001 | Peeters | |
| 6,355,431 B1 | 3/2002 | Chee et al. | |
| 6,426,231 B1 | 7/2002 | Bayley et al. | |
| 6,428,959 B1 | 8/2002 | Deamer | |
| 6,465,193 B2 | 10/2002 | Akeson et al. | |
| 6,617,113 B2 | 9/2003 | Deamer | |
| 6,627,067 B1 | 9/2003 | Branton et al. | |
| 6,746,594 B2 | 6/2004 | Akeson et al. | |
| 6,805,009 B2 | 10/2004 | Burdess et al. | |
| 6,824,659 B2 | 11/2004 | Bayley et al. | |
| 6,878,539 B1 | 4/2005 | Fritzsche et al. | |
| 6,916,665 B2 | 7/2005 | Bayley et al. | |
| 6,927,070 B1 | 8/2005 | Bayley et al. | |
| 6,977,171 B1 | 12/2005 | Dennis et al. | |
| 7,001,792 B2 | 2/2006 | Sauer et al. | |
| 7,015,701 B2 | 3/2006 | Wiegand et al. | |
| 7,048,844 B2 | 5/2006 | Chen et al. | |
| 7,060,507 B2 | 6/2006 | Akeson et al. | |
| 7,091,715 B2 | 8/2006 | Nemirovsky et al. | |
| 7,122,152 B2 | 10/2006 | Lewis et al. | |
| 7,129,554 B2 | 10/2006 | Lieber et al. | |
| 7,135,294 B2 | 11/2006 | Lee et al. | |
| 7,157,232 B2 | 1/2007 | Miles et al. | |
| 7,189,503 B2 | 3/2007 | Akeson et al. | |
| 7,195,780 B2 | 3/2007 | Dennis et al. | |
| 7,238,485 B2 | 7/2007 | Akeson et al. | |
| 7,248,771 B2 | 7/2007 | Schmidt et al. | |
| 7,258,838 B2 | 8/2007 | Li et al. | |
| 7,259,019 B2 | 8/2007 | Pawliszyn et al. | |
| 7,339,212 B2 | 3/2008 | Kawarada | |
| 7,381,316 B1 | 6/2008 | Lee et al. | |
| 7,385,267 B2 | 6/2008 | Liber et al. | |
| 7,393,644 B2 | 7/2008 | Lee et al. | |
| 7,452,669 B2 | 11/2008 | Kim et al. | |
| 7,646,045 B2 | 1/2010 | Kreupl et al. | |
| 7,648,844 B2 | 1/2010 | Srivastava et al. | |
| 2002/0050167 A1 | 5/2002 | Foote | |
| 2002/0072054 A1 | 6/2002 | Miles et al. | |
| 2002/0092363 A1 * | 7/2002 | Jorgenson et al. | 73/861.95 |
| 2002/0127760 A1 | 9/2002 | Yeh et al. | |
| 2004/0001778 A1 | 1/2004 | Chen et al. | |
| 2004/0136866 A1 | 7/2004 | Pontis et al. | |
| 2004/0238379 A1 * | 12/2004 | Lindsay et al. | 205/792 |
| 2005/0032100 A1 | 2/2005 | Heath et al. | |
| 2005/0079528 A1 | 4/2005 | Takiguchi et al. | |
| 2005/0082944 A1 | 4/2005 | Thompson et al. | |
| 2005/0095698 A1 | 5/2005 | Carlson | |
| 2005/0127035 A1 | 6/2005 | Ling | |
| 2005/0176051 A1 | 8/2005 | Fritzsche et al. | |
| 2005/0208574 A1 | 9/2005 | Bayley et al. | |
| 2005/0212014 A1 | 9/2005 | Horibe et al. | |
| 2005/0212016 A1 | 9/2005 | Brunner et al. | |
| 2005/0221362 A1 | 10/2005 | Takiguchi et al. | |
| 2006/0024802 A1 * | 2/2006 | Muller et al. | 435/173.1 |
| 2006/0035400 A1 | 2/2006 | Wu et al. | |
| 2006/0063171 A1 | 3/2006 | Akeson et al. | |
| 2006/0121501 A1 | 6/2006 | Jabs et al. | |
| 2006/0174683 A1 | 8/2006 | Bonne et al. | |
| 2006/0180898 A1 | 8/2006 | Funaki et al. | |
| 2006/0196253 A1 | 9/2006 | Crawley et al. | |
| 2006/0197118 A1 | 9/2006 | Migliorato et al. | |
| 2006/0228723 A1 | 10/2006 | Bradley et al. | |
| 2006/0246497 A1 * | 11/2006 | Huang et al. | 435/6 |
| 2006/0269927 A1 | 11/2006 | Lieber et al. | |
| 2007/0042366 A1 | 2/2007 | Ling | |
| 2007/0114573 A1 | 5/2007 | Han et al. | |
| 2007/0132043 A1 | 6/2007 | Bradley et al. | |
| 2007/0178470 A1 | 8/2007 | Bissonnette et al. | |
| 2007/0178477 A1 | 8/2007 | Joiner, Jr. et al. | |
| 2007/0190542 A1 | 8/2007 | Ling et al. | |
| 2007/0222011 A1 | 9/2007 | Robert et al. | |
| 2007/0235760 A1 | 10/2007 | Shim et al. | |
| 2007/0292855 A1 | 12/2007 | Dubin et al. | |
| 2008/0025875 A1 | 1/2008 | Martin et al. | |
| 2008/0108164 A1 | 5/2008 | Oleynik | |
| 2008/0164541 A1 | 7/2008 | Segal et al. | |
| 2008/0280776 A1 | 11/2008 | Bashir et al. | |
| 2009/0008629 A1 | 1/2009 | Matsumoto et al. | |
| 2009/0026082 A1 * | 1/2009 | Rothberg et al. | 204/556 |
| 2009/0061416 A1 | 3/2009 | Fang et al. | |
| 2009/0139340 A1 | 6/2009 | King et al. | |
| 2009/0142790 A1 | 6/2009 | Fang et al. | |
| 2009/0199639 A1 | 8/2009 | Konno et al. | |
| 2009/0288963 A1 | 11/2009 | Guerrieri et al. | |
| 2010/0026136 A1 | 2/2010 | Gaidarzhy et al. | |
| 2010/0068697 A1 | 3/2010 | Shih et al. | |
| 2010/0137143 A1 | 6/2010 | Rothberg et al. | |
| 2011/0086352 A1 | 4/2011 | Bashir et al. | |
| 2011/0226623 A1 | 9/2011 | Timp et al. | |
| 2012/0021918 A1 | 1/2012 | Bashir et al. | |

FOREIGN PATENT DOCUMENTS

| | | |
|---|---|---|
| WO | WO 93/08464 | 4/1993 |
| WO | WO 00/71981 | 11/2000 |
| WO | WO 2004/085609 | 10/2004 |
| WO | WO 2005/031300 | 4/2005 |
| WO | WO 2005/056827 | 6/2005 |
| WO | WO 2006/137891 | 12/2006 |
| WO | WO 2008/048222 | 4/2008 |
| WO | WO 2008/060713 | 5/2008 |
| WO | WO 2008/070058 | 6/2008 |
| WO | WO 2010/022285 | 2/2010 |
| WO | WO 2010/037085 | 4/2010 |
| WO | WO 2010/047804 | 4/2010 |
| WO | WO 2010/080617 | 7/2010 |
| WO | WO 2011/163058 | 12/2011 |
| WO | WO 2012/078340 | 6/2012 |

OTHER PUBLICATIONS

K. H. Jurgen Buschow et al. (Eds.) (2001), "Encyclopedia of Materials: Science and Technology", Elsevier Science Ltd., vol. 9, Re-S, pp. 8576-8584.

Modreanu et al. (2003), "Dielectrics in Emerging Technologies: Optical Characterisation of LPCVD $SiO_xN_y$ Thin Films", Electrochemical Society Proceedings vol. 2003-01, pp. 118-122.

"International Technology Roadmap for Semiconductors, 2006 Update, Overview and Working Group Summaries," *ITRS* 2006.

Adkins et al. (2002) "Toward a Human Blood Serum Proteome," *Mol. Cell Proteom.* 1:947-955.

Afanas'ev et al. (Sep. 1, 1997) "Structural Inhomogeneity and Silicon Enrichment of Buried $SiO_2$ Layers Formed by Oxygen Ion Implantation in Silicon," *J. Appl. Phys.* 82(5):2184-2199.

Ajikumar et al. (2006) "Design, Fabrication and Functional Analysis of a new Protein Array Based on ssDNA-Based Assembly," *MIT Libraries*.

Akeson et al. (Dec. 1999) "Microsecond Time-Scale Discrimination Among Polycytidylic Acid, Polyadenylic Acid, and Polyuridylic Acid as Homopolymers or as Segments Within Single RNA Molecules," *Biophys. J.* 77:3227-3233.

Akin et al. (Web Release Jun. 10, 2007) "Bacterial-Mediated Delivery of Nanoparticles in Cells," *Nat. Nanotechnol.* 149:441-449.

Albrecht et al. (Oct. 2004) "Geometric and material determinants of patterning efficiency by dielectrophoresis." *Biophys. J.* 87(4):2131-2147.

Andelman, D. (Nov. 24, 2004) "Introduction to Electrostatics in Soft and Biological Matter," *School of Physics and Astronomy* 24pp.

Anderson et al. (1969) "Cell Growth and Division. IV. Determination of Volume Growth Rate and Division Probability," *Biophys J.* 9:246-263.

Anderson et al. (1970). "Density invariance of cultured Chinese hamster cells with stage of the mitotic cycle." *Biophys J* 10(7): 630-645.

(56) References Cited

OTHER PUBLICATIONS

Anderson, M. (1999) "Solution Hybridization: Reassociation of DNA," *Nucleic Acid Hybridization*, Springer, Berlin, pp. 17-33.

Andersson et al. (2003) "Microfluidic Devices for Cellomics: A Review," *Sens. Actuators B* 92:315-325.

Antonik et al. (1997). "A biosensor based on micromechanical interrogation of living cells." *Ieee Eng. Med. Biol. Mag.* 16(2): 66-72.

Antony et al. (Feb. 5, 1989) "Identification of a MG2+-Dependent Protease in Human Placenta Which Cleaves Hydrophobic Folate-Binding Proteins to Hydrophilic Forms," *J. Biol. Chem.* 264(4):1911-1914.

Antony, A.C. (1996) "Folate Receptors," *Ann. Rev. Nutr.* 16:501-521.

Arata et al. (Oct. 12, 2006) "Temperature Distribution Measurement on Microfabricated Thermodevices for Single Biomolecular Observation Using Fluorescent Dye," *Sens. Act. B*. 117(2):339-345.

Argaman et al. (Nov. 1, 1997) "Phase Imaging of Moving DNA Molecules and DNA Molecules Replicated in the Atomic Force Microscope," *Nu. Acids Res.* 25(21):4279-4384.

Ashcroft et al. (2004) "Calibration of a pH Sensitive Buried Channel Silicon-on-Insulator MOSFET for Sensor Applications," *Phys. Stat. Sol.* 241(10):2291-2296.

Asmann et al. (Jun. 1, 2002) "Identification of Differentially Expressed Genes in Normal and Malignant Prostate by Electronic Profiling of Expressed Sequence Tags," *Cancer Res.* 62:3308-3314.

Astier et al. (2006) "Toward Single Molecule DNA Sequencing: Direct Identification of Ribonucleoside and Deoxyribonucleoside 5'-Monophosphates by Using an Engineered Protein Nanopore Equipped with a Molecular Adapter," *J. Am. Chem. Soc.* 128:1705-1710.

Bae et al. (2005) "Study on Orientation of Immunoglobulin G on Protein G Layer," *Biosens and Bioelectron.* 21:103-110.

Bai et al. (2006) "Single-Molecule Analysis of RNA Polymerase Transcription," *Ann. Rev. Biophys. Biomot Struct.* 35:343-360.

Bajaj et al. (2007) "Ulrananocrystalline Diamond Film as an Optimal Cell Interface for Biomedical Applications," *Biomed. Microdev.* 9(6):787-794.

Baker et al. (Aug. 28, 2001) "Electrostatics of Nanosystems: Application to Microtubules and the Ribosome," *Proc. Nat. Acad. Sci. USA* 98:10037-10041.

Baker-Jarvis et al. (1998) "Electrical Properties and Dielectric Relaxation of DNA in Solution," *NIST Technical Note* 1509.

Bakker, E. (2004) "Electrochemical Sensors," *Anal. Chem.* 76:3285-3298.

Banada et al. (Aug. 15, 2006) "Performance Evaluation of a Low Conductive Growth Medium (LCGM) for Growth of Healthy and Stressed *Listeria monocytogenes* and Other Common Bacterial Species," *Int. J. Food Microbiol.* 111(1):12-20.

Baranski et al. (2002) "Hot Microelectrodes," *Anal. Chem.* 74:1294-1301.

Bashir et al. (2004) "BioMEMS: State-of-the-Art-in Detection, Opportunities and Prospects," *Adv. Drug. Deliv. Rev.* 56(11):1565-1586.

Bauer et al. (Aug. 1, 2006) "Molecular Transport Through Channels and Pores: Effects of In-Channel Interactions and Blocking," *Proc. Nat. Acad. Sci. USA* 103:11446-11451.

Bates et al. (Apr. 2003) "Dynamics of DNA Molecules in a Membrane Channel Probed by Active Control Techniques," *Biophys. J.* 84:2366-2372.

Baumann et al. (Apr. 25, 1999) "Microelectronic Sensor System for Microphysiological Application on Living Cells," *Sens.Act.B* 55(1):77-89.

Becker et al. (Jan. 1995) "Separation of Human Breast Cancer Cells from Blood by Differential Dielectric Affinity," *Proc. Nat. Acad. Sci. USA* 92:860-864.

Belgrader et al. (Apr. 16, 1999) "PCR Detection of Bacteria in Seven Mniutes," *Science* 284:449-450.

Benner et al. (Web Release Oct. 27, 2007) "Sequence-specific detection of individual DNA polymerase complexes in real time using a nanopore," *Nat. Nanotechnol.* 2:718-724.

Berdat et al. (Oct. 25, 2006) "DNA Biosensor Using Fluorescence Microscopy and Impedance Spectroscopy," *Sensors and Actuators B* 118(1-2):53-59.

Berezhkovskii et al. (2005) "Optimizing Transport of Metabolites Through Large Channels: Molecular Sieves With and Without Binding," *Biophys. J.* 88:L17-L19.

Bergveld, P. (Jan. 1970) "Development of an Ion-Sensitive Solid-State Device for Neutophysiological Measurements," *IEEE Trans. Biomed. Eng.* 17(1):70-71.

Bergveld, P. (Sep. 1972) "Development, Operation, and Application of the Ion-Sensitive Field-Effect Transistor as a Tool for Electrophysiology," *IEEE Trans. Biomed. Eng.* 19(5):342-351.

Bergveld, P. (1991) "A Critial Evaluation of Direct Electrical Protein Detection Methods," *Biosens. Bioelectron.* 6(1):55-72.

Bergveld, P. (2003) "Thirty Years of ISFETOLOGY What Happened in the Past 30 Years and What May Happen in the Next 30 Years," *Sens. Actuators B* 88:1-20.

Berman et al. (2000) "The Protein Data Bank," *Nuc. Acids Res.* 28(1):235-242.

Bertrand (1994) "Induction of a common pathway of apoptosis by staurosporine," *Exp. Cell Res.* 211(2):314-321.

Bhatia et al. (1992) "New Approach to Producing Patterned Biomolecular Assemblies," *J. Am. Chem. Soc.* 114::4432-4433.

Bhattacharya et al. (2007) "Biomems and Nanotechnology Based Approaches for Rapid Detection of Biological Entities," *J.f Rapid Methods Automation Microbiol.* 15:1-32.

Bhattacharya et al. (2008) "PCR-Based Detection in a Micro-Fabricated Platform," *Lab Chip*. 8:1130-1136.

Bhowmick et al. (Web Release Dec. 18, 2008) "Dielectric Scaling of a Top Gate Silicon Nanowire on Insulator Transistor," *J. Appl. Phys.* 104(12):124308.

Bicore® Product Information (2001) "The Versatile High Sensitivity System," http://web.bf.uni-lj.si/bi/sprcenter/BiacoreX.pdf, 8pp.

Bilbo et al. (Aug. 24,2009) "Early-life programming of later-life brain and behavior: a critical role for the immune system." *Front Behav Neurosci* 3® Article 14) 14pp.

Blatt et al. (2001). "Signaling pathways and effector mechanisms pre-programmed cell death." *Bioorg Med Chem* 9(6):1371-1384.

Blawas et al. (1998) "Protein Patterning," *Biomaterials* 19:595-609.

Boerman et al. (1991) "Comparative Immunochemical Study of Four Monoclonal Antibodies Directed Against Ovarian Carcinoma-Associated Antigens," *Int. J. Gynecol. Pathol.* 10:15-25.

Boozer et al. (2006) "Looking Towards Label-Free Biomolecular Interaction Analysis in a High-Throughput Format: A Review of New Surface Plasmon Resonance Technologies," *Curr. Opin. Biotechnol.* 17:400-405.

Borsenberger et al. (2009) "Chemically Labeled Nucleotides and Oligonucleotides Encode DNA for Sensing with Nanopores," *J. Am. Chem. Soc.* 131:7530-7531.

Botstein et al. (Mar. 2003) "Discovering genotypes underlying human phenotypes: past successes for mendelian disease, future approaches for complex disease," *Nat. Genet.* 33:228-237.

Bousse et al. (Oct. 1983) "Operation of Chemically Sensitive Field-Effect Sensors as a Function of the Insulator-Electrolyte Interface," *IEEE Trans. Elec. Dev.* 30(10):1263-1270.

Brainkley et al. (1977) "The Curability of Breast Cancer," *World J. Surg.* 1:287-289.

Brandt et al. (2003) "PNA Microarrays for Hybridisation of Unlabeled DNA Samples," *Nuc. Acids. Res.* 31(19):e119.

Branton et al. (Oct. 2008) "The potential and challenges of nanopore sequencing," *Nat. Biotechnol.* 26(10):1146-1153.

Braun et al. (Sep. 14, 2005) "Micromechanical mass sensors for biomolecular detection in a physiological environment." *Physical Review E* 72(3):031907.

Brinkley et al. (Jul. 19, 1975) "The Curability of Breast Cancer," *Lancet* 306(7925):95-97.

Briones et al. (Nov. 2004) "Ordered Self-Assembled Monolayers of Peptide Nucleic Acids with DNA Recognition Capability," *Phys. Rev. Lett.* 93(20):208103.

Brooks et al. (Jan. 1985) "Cell Growth, Cell Division and Cell Size Homeostasis in Swiss 3T3 Cells," *Exp. Cell Res.* 156:1-6.

(56) References Cited

OTHER PUBLICATIONS

Brown et al. (Oct. 1994) "Moat Edge Oriented Defects and Buried Oxide Leakage in Simox Integrated Circuits," *Proceedings 1994 IEEE International SOI Conference* :133-134.

Brown, G.A. (Sep. 1993) "Defect Electrical Conduction in SIMOX Buried Oxides," *IEEE Trans. Electron Dev.* 40(9):1700-1705.

Bryan et al. (Jan. 19, 2010) "Measurement of Mass, Density, and Volume During the Cell Cycle of Yeast," *Proc. Nat. Acad. Sci. U.S.A.* 107(3):999-1004.

Bunimovich et al. (Web Release Oct. 15, 2004) "Electrochemically Programed, Spatially Selective Biofunctionalization of Silicon Wires," *Langmuir* 20:10630-10638.

Bunimovich et al. (2006) "Quantitative Real-Time Measurements of DNA Hybridization with Alkylated Nonoxidized Silicon Nanowires in Electrolyte Solution,"*J. Am. Chem. Soc.*128:16323-16331.

Burg et al. (Sep. 29, 2003) "Suspended microchannel resonators for biomolecular detection." *Appl. Phys. Lett.* 83(13):2698-2700.

Burg et al. (Dec. 2006) "Vacuum-packaged suspended microchannel resonant mass sensor for biomolecular detection." *J. Microelectromech. Syst.* 15(6):1466-1476.

Burg et al. (Apr. 26, 2007) "Weighing of biomolecules, single cells and single nanoparticles in fluid." *Nature* 446 (7139):1066-1069.

Burg et al. (Jun. 2009) "Nonmonotonic energy dissipation in microfluidic resonators." *Phys Rev Lett* 102(22):228103.

Burns et al. (Oct. 16, 1998) "An Integrated Nanolited DNA Analysis Device," *Science* 282:484-487.

Cady et al. (Web Release Dec. 8, 2004) "Real-Time PCR detection of *Listeria monocytogenes* using and integrated microfluidics platform," *Sensors Actuators B* 107:332-341.

Calin et al. (Nov. 2006) "MicroRNA signatures in human cancers," *Nat. Rev. Cancer* 6:857-866.

Campbell et al. (Oct. 1, 1991) "Folate-Binding Protein is a Marker for Ovarian Cancer," *Cancer Res.* 51:5329-5338.

Casalini et al. (2004) "Role of HER Receptors Family in Development and Differentiation," *J. Cell. Phys.* 200:343-350.

Chamsart et al. (2001) "The Impact of Fluid-Dynamic-Generated Stresses on chDNA and pDNA Stability During Alkaline Cell Lysis for Gene Therapy Products," *Biotechnol. Bioeng.* 75(4):387-392.

Chandler et al. (2003) "Enhanced Nucleic Acid Capture and Flow Cytometry Detection with Peptide Nucleic Acid Perobes and Tunable-Surface Microparticles," *Anal. Biochem.* 312:182-190.

Chang et al. (2003) "Poly(dimethyllsiloxane) PDMS and Silicon Hybrid Biochip for Bacterial Culture," *Biomed. Microdev.* 5(4):281-290.

Chang et al. (2004) "DNA-Mediated Fluctuations in Ionic Current through Silicon Oxide Nanopore Channels," *Nano Lett.* 4(8):1551-1556.

Chang et al. (2006) "Fabrication and Characterization of Solid State Nanopores Using Field Emission Scanning Electron Beam," *Appl. Phys. Lett.* 88(10):103109.

Chang et al. (Sep. 2006) "DNA Counterion Current and Saturation Examined by a Solid State Nanopore Sensor," *Biomedical MicroDevices* 8(3):263-269.

Chen et al. (May 1996) "Identification and Differentiation of *Mycobacterium avium* and *M. intreacellulare* by PCR," *J. Clin. Microbiol.* 34(5):1267-1269.

Chen et al. (2004) "Probing Single DNA Molecule Transport Using Fabricated Nanopores," *Nano Lett.* 4(11):2293-2298.

Chen et al. (Web Release Nov. 29, 2006) "Silicon-Based Nanoelectronic Field-Effect *p*H Sensor with Local Gate Control," *Appl. Phys. Lett.* 89(22):223512.

Chen et al. (Web Release Dec. 14, 2007) "Nanoscale Field Effect Transsitor for Biomolecular Signal Amplification," *Appl. Phys. Lett.* 91(24):243511.

Chen et al. (Aug. 2010) "DNA translocation through an array of kinked nanopores," *Nat. Mater.* 9:667-675.

Chen et al. (Web Release Oct. 26, 2009) "Top-Down Fabrication of Sub-30 nm Monocrystalline Silicon Nanowires Using Conventional Microfabrication," *ACS Nano* 3(11):3485-3492.

Cheng et al. (2007) "A Microfluidic Device for Practical Label-Free CD4+ T Cell Counting of HIV-Infected Subjects," *Lab Chip* 7:170-178.

Cheng et al. (Jun. 2007) "Cell Detection and Counting Through Cell Lysate Impedance Spectroscopy in Microfluidic Devices," *Lab Chip* 7:746-755.

Choi et al. (2007) "A Cellular Trojan Horse for Delivery of Therapeutic Nanoparticles into Tumors," *Nanolett.* 7(12):3759-3765.

Chrisey et al. (1996) "Covalent Attachment of Synthetic DNA to Self-Assembled Monolayer Films," *Nuc. Acids Res.* 24(15):3031-3039.

Chua et al. (Web Release Jul. 10, 2009) "Label—Free Eletrical Detection of Cardiac Biomarker with Complementary Metal-Oxide Semiconductor-Compatible Silicon Nanowire Sensor Arrays," *Anal. Chem.* 81(15):6266-6271.

Chung et al. (2011) "Stability of DNA-Tethered Lipid Membranes with Mobile Tethers," *Langmuir* 27:5492-5497.

Circu et al. (2009) "The role of GSH efflux in staurosporine-induced apoptosis in colonic epithelial cells", *Biochem. Pharmacol.*, 77(1):76-85.

Clarke et al. (Web Release Feb. 22, 2009) "Continuous base identification for single-molecule nanopore DNA sequencing," *Nat. Nanotechnol.* 4:265-270.

Cockroft et al. (2008) "A Single-Molecule Nanopore Device Detects DNA Polymerase Activity with Single-Nucleotide Resolution," *J. Am. Chem. Soc.* 130:818-820.

Cohen-Karni et al. (2009) "Flexible Electrical Recording From Cells Using Nanowire Transistor Arrays," *Proc. Nat. Acad. Sci. USA* 106(18):7309-7313.

Compton J. (Mar. 7, 1991) "Nucleic acid sequence-based amplification," *Nature* 350(6313):91-92.

Conlon et al. (Web Release Apr. 24, 2003) "Differences in the Way a Mammalian Cell and Yeast Cells Coordinate Cell Growth and Cell-Cycle Progression," *J. Biol.* 2(1):7.

Conlon et al. (Web Release Sep. 12, 2001) "Extracellular Control of Cell Size," *Nat. Cell Biol.* 3:918-921 Including Correction and Erratum.

Cooper (2006) "Distinguishing Between Linear and Exponential Cell Growth During the Division Cycle: Single-Cell Studies, Cell-Culture Studies, and the Object of Cell-Cycle Research," *Theor. Biol. Med. Model.* 3:10.

Cooper, M.A. (2003) Label-Free Screening of Bio-Molecular Interactions,: *Anal. Bioanal. Chem.* 377:834-842.

Cooper, S. (Feb. 23, 2006) "Distinguishing Between Linear and Exponential Cell Growth During the Division Cycle: Single-Cell Studies, Cell-Culture Studies, and the Object of Cell-Cycle Research," *Theor. Biol. Med. Model* 3:47, 15 pp.

Crooke et al. (Web Release Mar. 18, 2009) "PLC-gamma1 regulates fibronectin assembly and cell aggregation." *Exp Cell Res* 315(13): 2207-2214.

Cui et al. (2001) "Electrothermal Modeling of Silicon PCR Chips," *Proceedings of SPIE* 4407:275-280.

Cui et al. (Aug. 17, 2001) "Nanowire Nanosensors for Highly Sensitive and Selective Detection of Biological and Chemical Species," *Science* 293:1289-1292.

Curreli et al. (2005) "Selective Functionalization of $In_2O_3$ Nanowire Mat Devices for Biosensing Applications," *J. Am. Chem. Soc.* 127:6922-6923.

Dankerl et al. (2008) "Revsolving the Controversy of the pH Sensitivity of Diamond Surfaces," *Physica Status Solidi-Rapid Res. Lett.* 2(1):31-33.

Das et al. (Web Release May 2, 2006) "A defined system to allow skeletal muscle differentiation and subsequent integration with silicon microstructures." *Biomaterials* 27(24): 4374-4380.

Das et al. (2007) "Differentiation of skeletal muscle and integration of myotubes with silicon microstructures using serum-free medium and a synthetic silane substrate." *Nat Protoc* 2(7): 1795-1801.

Davila et al. (Web Release Jan. 25, 2007) "Microresonator mass sensors for detection of *Bacillus anthracis* Sterne spores in air and water." *Biosens.Bioelectron.* 22(12): 3028-3035.

De Caterina et al. (2002) "Effects of Paraformaldehyde on Platelet Size and on Measurement of Surface IgG," *Platelets* 13(4):207-212.

(56) References Cited

OTHER PUBLICATIONS de Vries et al. (Web Release Apr. 24, 2007) "Direct Observation of Nanomechanical Properties of Chromatin in Living Cells," *Nano Lett.* 7(5):1424-1427.

Deamer (2002) "Characterization of Nucleic Acids by Nanopore Analysis," *Acc. Chem. Res.* 35:817-825.

Deamer, D.W. (2010) Nanopore analysis of nucleic acids bound to exonucleases and polymerases. *Annu Rev Biophys* 39:79-90.

Dekker, C. (Apr. 2007) "Solid-state nanopores," *Nat. Nanotechnol.* 2:209-215.

Derrington et al. (Sep. 14, 2010) Nanopore DNA sequencing with MspA. *Proc. Natl Acad. Sci. USA* 107(:16060-16065.

Dohn et al. (2007) "Mass and position determination of attached particles on cantilever based mass sensors," *Rev. Sci. Instrum.* 78(10):103303.

Dohn et al. (2005) "Enhanced functionality of cantilever based mass sensors using higher modes," *AppL Phys. Lett.*, 86:233501.

Drmanac et al. (Jan. 1, 2010) Human Genome Sequencing Using Unchained Base Reads on Self-Assembling DNA Nanoarrays. *Science* 327:78-81.

Drmanac et al. (Jan. 1998) "Accurate Sequencing by Hybridization for DNA Diagnosis and Individual Genomics," *Nature Biotechnol.* 16:54-58.

Echave et al. (Jan. 15, 2007) "Cell Size Regulation in Mammalian Cells," *Cell Cycle* 6(2):218-224.

Eid et al. (Jan. 2, 2009) "Real-Time DNA Sequencing from Single Polymerase Molecules.,"*Science* 323:133-138.

Ekinci et al. (Mar. 2004) "Ultimate limits to inertial mass sensing based upon nanoelectromechanical systems." *Journal of Applied Physics* 95(5): 2682-2689.

El-Ali et al. (2004) "Simulation and experimental validation of a SU-8 based PCR thermocycler chip with integrated heaters and temperature sensor," *Sens. Actuators A* 110:3-10.

Elfstrom et al. (Web Release Aug. 11, 2007) "Surface Charge Sensitivity of Silicon Nanowires: Size Dependence," *Nano Letters* 7(9):2608-2612.

Elfstrom et al. (2008) "Biomolecule Detection Using a Silicon Nanoribbon: Accumulation Mode Versus Inversion Mode," *Nanotechnology* 19(23):235201.

Elfstrom et al. (Web Release Feb 12, 2008) "Silicon Nanoribbons for Electrical Detection of Biololecules," *Nano Letters* 8(3):945-949.

Elibol et al. (2007) "Selective Heating Characterization of Nanoplate Devices for Sensing Applications," *NSTI-Nanotech* 2:198-201.

Elibol et al. (2009) "Localized Heating on Silicon Field Effect Transistors: Device Fabrication and Temperature Measurements in Fluid," *Lab on Chip* 9(19):2789-2795.

Elibol et al. (Dec. 1, 2003) "Integrated Nanoscale Silicon Sensors using Top-Down Fabrication," *Appl. Phys. Lett.* 83(22):4613-4615.

Elibol et al. (Web Release May 15, 2008) "Nanoscale Thickness Double-Gated Field Effect Silicon Sensors for Sensitive $p$H Detection in Fluid," *Appl. Phys. Lett.* 92(19):193904.

Elibol et al. (Web Release Sep. 30, 2008) "Localized Heating and Thermal Characterization of High Electrical Resistivity Silicon-on-Insulator Sensors Using Liquid Crystals," *Appl. Phys. Lett.* 93(13):131908.

Elliott et al. (Sep. 1978) "Rate of Macromolecular Synthesis Through the Cell Cycle of the Yeast *Saccharomyces cerevisiae*," *Proc. Nat. Acad. Sci. U.S.A.* 75(9):4384-4388.

Faller et al. (Feb. 20, 2004) "The Structure of a Mycobacterial Outer-Membrane Channel," *Science* 303:1189-1192.

Faraudo, J. (Dec 30, 2002) "New Cooperative Effects in Ballistic Deposition of Hard Disks," *Phys. Rev. Lett.* 89(27):276104-276111.

Feldman et al. (Jan. 20, 2011) "Discovery of recurrent t(6;7)(p25.3;q32.3) translocations in ALK-negative anaplastic large cell lymphomas by massively parallel genomic sequencing," *Blood* 117(3):915-919.

Fischbein et al. (2008) "Electron beam nanosculpting of suspended graphene sheets.," *Appl. Phys. Lett.* 93(11):113107-113103.

Fischer et al. (2003). "Many cuts to ruin: a comprehensive update of caspase substrates." *Cell Death Differ* 10(1): 76-100.

Fodor et al. (Feb. 15, 1991) "Light-Directed, Spatially Addressable Parallel Chemical Synthesis," *Science* 251(4995):767-773.

Fologea et al. (2005) "Slowing DNA Translocation in a Solid-State Nanopore," *Nano Lett.* 5(9):1734-1737.

Fox et al. (1985) "Formaldehyde Fixation," *J. Histochem. Cytochem.* 33(8):845-853.

Fritz et al. (Oct. 29, 2002) "Electronic Detection of DNA by its Intrinsic Molecular Charge," *Proc. Nat. Acad. Sci USA* 99(22):14142-14146.

Fung et al. (Jan. 1986) "A Generalized Theory of an Electrolyte-Insulator-Semiconductor Field-Effect Transistor," *IEEE Trans. Elctron. Dev.* 33(1):8-18.

Gabriel et al. (1998) "Dielectric Parameters Relevant to Microwave Dielectric Heating," *Chem. Soc. Rev.* 27:213-223.

Gambino et al. (1998) "Silicides and ohmic Contacts," *Mater. Chem. Phys.* 52:99-146.

Gao et al. (Web Release Jun. 6, 2006) "Secondary Structure Effects on DNA Hybridization Kinetics: A Solution Versus Surface Comparison," *Nuc. Acids Res.* 34(11):3370-3377.

Gao et al. (2007) "Silicon Nanowire Arrays for Ulta-Sensitive label-Free Detection of DNA," *Proc. $14^{th}$ International Conference on Solid-State Sensors, Actuators, and Microsystems*, pp. 2003-2006.

Gao et al. (Web Release Apr. 4, 2007) "Silicon Nanowire Arrays for Label-Free Detection of DNA," *Anal. Chem.* 79(9):3291-3297.

Gao et al. (Web Release Nov. 12, 2009) "Subthreshold Regime has the Optimal Sensitivity for Nanowire FET Biosensors," *Nano Letters* 10(2):547-552.

Garaj et al. (2010) "Graphene as a subnanometre trans-electrode membrane," *Nature* 467:190-193.

Ge et al. (May 2006) "Thermal Conductance of Hydrophilic and Hydrophobic Interfaces," *Phys. Rev. Lett.* 96:186101.

Geim, A.K. (Jun. 19, 2009) "Graphene: Status and Prospects," *Science* 324:1530-1534.

George, S.M. (2009) "Atomic Layer Deposition: An Overview," *Chem. Rev.* 110:111-131.

Gfeller et al. (2005). "Micromechanical oscillators as rapid biosensor for the detection of active growth of *Escherichia coli*." *Biosens. Bioelectron.* 21(3): 528-533.

Girit et al. (Mar. 27, 2009) "Graphene at the Edge: Stability and Dynamics," *Science* 323:1705-1708.

Gnani et al. (Jan. 2007) "Effects of High-Kappa (HfO2) Gate Dielectrics in Double-Gate and Cylindrical-Nanowire FETs Scaled to the Ultimate Technology Nodes," *IEEE Trans. Nanotechnol.* 6(1):90-96.

Godin et al. (May 2010) "Using buoyant mass to measure the growth of single cells", *Nat. Methods.* 7(5):387-390.

Gomez et al. (2002) "Microscale Electronic Detection of Bacterial Metabolism," *Sens. Actuators B* 86:198-208.

Gomez et al. (2007) "Immobilized nerve growth factor and microtopography have distinct effects on polarization versus axon elongation in hippocampal cells in culture." *Biomaterials* 28(2): 271-84.

Gomez et al. (Sep. 14, 2001) "Micro-Fluidic Biochip for Impedance Spectroscopy of Biological Species," *Biomed. Micr-Dev.* 3(3):201-209.

Gomez-Sjoberg et al. (Aug. 2005) "Impedance Microbiology-on-a-Chip: Microfluidic Bioprocessor for Rapid Detection of Bacterial Metabolism," *IEEE/ASME Journal of Microelectromechanical Syst.* 14(4):829-838.

Gracheva et al. (2006) "Simulation of the electric response of DNA translocation through a semiconductor nanopore-capacitor," *Nanotechnology* 17:622-633.

Grahame, D.C. (1947) "The Electrical Double Layer and the Theory of Electrocapillarity," *Chem. Rev.* 41:441-501.

Greulich, K.O. (Dec. 5, 2005) "Review: Single Molecule Studies on DNA and RNA," *ChemPhysChem* 6:2458-2471.

Groisman et al. (Sep. 2005). "A microfluidic chemostat for experiments with bacterial and yeast cells." *Nature Methods* 2(9): 685-689.

Groves et al. (Jan. 31, 1997) "Micropatterning fluid lipid bilayers on solid supports," *Science* 275:651-653.

Gu et al (Apr. 22, 1999) "Stochastic Sensing or Organic Analytes by a Pore-forming Protein Containing a Molecular Adapter," *Nature* 398:686-690.

(56) References Cited

OTHER PUBLICATIONS

Guiducci et al. (Oct. 2006) Micoelectrodes on a Silicon Chip for Label-Free Capacitive DNA, *IEEE Sensors J.* 6(5):1084-1093.
Gupta et al. (Apr. 2003) "Novel fabrication method for surface micromachined thin single-crystal silicon cantilever beams." *Journal of Microelectromechanical Systems* 12(2):185-192.
Gupta et al. (Nov./Dec. 2004) "Detection of bacterial cells and antibodies using surface micromachined thin silicon cantilever resonators." *Journal of Vacuum Science & Technology B* 22(6):2785-2791.
Gupta et al. (Mar. 15, 2004) "Single Virus Particle Mass Detection Using Mocroresonators with Nanoscale Thickness," *AppL Phsy. Lett.* 84(11):1976-1978.
Gupta et al. (Sep. 5, 2006) "Anomalous Resonance in a Nanomechanical Biosensor," *Proc. Nat. Acad. Sci. USA* 103(36):13362-13367.
Hadd et al. (Oct. 13, 2000) "Sub-Microliter DNA Sequencing for Capillary Array Electrophoresis," *J. Chromatogr. A* 894:191-201.
Hahm et al. (2004) "Direct Ultrasensitive Electrical Detection of DNA and DNA Sequence Variations Using Nanowire Nanosensors," *Nano Lett.* 4(1):51-54.
Hall et al. (Dec. 2010) "Hybrid pore formation by directed insertion of alpha-haemolysin into solid-state nanopores," *Nat. Nanotechnol.* 5:874-877.
Hall, J.E. (1975) "Access resistance of a small circular pore," *J. Gen. Physiol.* 66:531532.
Hamaguchi et al. (2001) "Aptamer Beacons for the Direct Detection of Proteins," *Anal. Biochem.* 294:126-131.
Hanss (Sep. 1973) "Dielectric Relaxation and Orientation of DNA Molecules," *Biopolymers*, 12(9):2151-2159.
Hashimoto et al. (Apr. 15, 2006) "Polymerase Chain Reaction/Ligase Detection Reaction/Hybridization Assays Using Flow-Through Microfluidic Devices for the Detection of Low-Abundant DNA Point Mutations," *Biosens.Bioelectron.* 21(10):19151923.
Healy et al. (2007) "Solid-state nanopore technologies for nanopore-based DNA analysis," *Nanomedicine* 2(6):875-897.
Healy, K. (2007) "Nanopore-based single-molecule DNA analysis," *Nanomedicine* 2(4):459-481.
Heitzinger et al. (2007) "Computational Aspects of the Three-Dimensional Feature-Scale Simulation of Silicon-Nanowire Field-Effect Sensors for DNA Detection," *J. Comput. Electron.* 6:387-390.
Heng et al. (2005) "Beyond the gene chip," *Bell Labs Tech. J.* 10:5-22.
Hong et al. (2004) "A Dielectric Biosensor Using the Capacitance Change with AC Frequency Integrated on Glass Substrates," *Japan. J. of Applied Physics*, 43:5639-5645.
Hoogerheide et al. (2009) "Probing Surface Charge Fluctuations with Solid-State Nanopores," *Phys. Rev. Lett.* 102:256804.
Hou et al. (2007) "Integrated Microelectronic Device for Label-Free Nucleic Acid Amplification and Detection," *Lab Chip* 7:347-354.
Hou et al. (Oct. 31, 2008) "Energy Uptake and Allocation During Ontogeny," *Science* 322(5902):736-739.
Howorka et al. (Jul. 2001) "Sequence-specific detection of individual DNA strands using engineered nanopores," *Nat. Biotech.* 19:636-639.
Hu et al. (Oct. 23, 2009) "Novel mechanisms of fibroblast growth factor receptor 1 regulation by extracellular matrix protein anosmin-1." *J Biol Chem* 284(43):29905-29920.
Huang et al. (2006) "An integrated microfluidic chip for DNA/RNA amplification, electrophoresis separation and on-line optical detection," *Electrophoresis* 27:3297-3305.
Huang et al. (2006) "Surface Directed Boundary Flow in Microfluidic Channels," *Langmuir* 22(14):6429-6437.
Huang et al. (Dec. 2010) "Identifying single bases in a DNA oligomer with electron tunneling," *Nat. Nanotechnol.* 5:868-873.
Huber et al. Jul. 18, (2003) "Programmed Adsorption and Release of Proteins in a Microfluidic Device," *Science* 310:352-354.
Iborra et al. (2008). "Wide confocal cytometry: a new approach to study proteomic and structural changes in the cell nucleus during the cell cycle." *Histochem Cell Biol* 129(1):45-53.
Iles et al. (Web Release Mar. 22, 2005) "Thermal Optimisation of the Reimer-Tiemann Reaction Using Thermochromic Liquid Crystals on a Microfluidic Reactor," *Lab Chip* 5:540-544.
Ilic et al. (2000) "Topographical patterning of chemically sensitive biological materials using a polymer-based dry lift off." *Biomed. Microdevices.* 2: 317-322.
Ilic et al. (Nov./Dec. 2001) "Single cell detection with micromechanical oscillators", *J. Vac. Sci. Technol. B*, 19(6):2825-2828.
Illanes et al. (2003) "Enzyme Reactor Design Under Thermal Inactivation," *Crit. Rev. Biotechnol.* 23(1):61-93.
Iniguez et al. (Dec. 1999) "A Physically-Based $C_\infty$-Continuous Model for Accumulation-Mode SOI pMOSFETs," *IEEE Trans. Electron Dev.* 46(12):2295-2303.
International Search Report and Written Opinion, Corresponding to International Application No. PCT/US2009/058739, Mailed Nov. 19, 2009.
International Search Report and Written Opinion, Corresponding to International Application No. PCT/US07/24804, Mailed Apr. 3, 2008.
International Search Report and Written Opinion, Corresponding to International Application No. PCT/US2011/040736, Mailed Dec. 12, 2011.
International Search Report and Written Opinion, Corresponding to International Application No. PCT/US2011/061524, Mailed Mar. 13, 2012.
Iqbal et al. (2005) "Direct Current Electrical Measurement of dsDNA Nanogap Junctions," *AppL Phys. Lett.* 86(15):153901.
Iqbal et al. (Web Release Apr. 1, 2007) "Solid State Nanopore Channels with DNA Selectivity," *Nat. Nanotechnol.* 2:243-248, Plus Supplementary Online Material.
Ivanov et al. (2010) "DNA Tunneling Detector Embedded in a Nanopore," *Nano Lett.* 11:279-285.
Jang et al. (Jan. 1999) "A Novel Approach for Modeling Accumulation-Mode SOI MOSFETs," *Solid-State Electronics* 43(1):87-96.
Jin et al. (2011) "Gated transport in nanofluidic devices," *Microfluid. Nanofluid.* 11:297-306.
Jing et al. (Web Release Aug. 19, 2010) "One-Way Traffic of a Viral Motor Channel for Double-Stranded DNA Translocation," *Nano Lett.* 10:3620-3627.
Joachim et al. (1994) "Analytical Modeling of Short-Channel Behavior of Accumulation-Mode Transistors on Silicon-on-Insulator Substrate," *Jap. J. Appl. Phys.* 33:558-562.
Johnson et al. (2006). "Characterization of vaccinia virus particles using microscale silicon cantilever resonators and atomic force microscopy." *Sensors and Actuators B-Chemical* 115(1): 189-197.
Jorgensen et al. (Web Release Dec. 13, 2004) "How Cells Coordinate Growth and Division," *Curr. Biol.* 14(23):R1014-R1027.
Juhasz et al. (Web Release Dec. 24, 2005) "Controlled Fabrication of Silicon Nanowires by Electron Beam Lithography and Electrochemical Size Reduction," *Nano Letters* 5(2):275-280.
Jülicher et al. (Mar. 1998) "Motion of RNA Polymerase Along DNA: A Stochastic Model," *Biophys. J.* 74:1169-1185.
Jungner et al. (May 28, 1949) "Molecular Weight Determination on Thymonucleic Acid Compounds by Dielectric Measurements," *Nature* 163:849-850.
Kajiyama et al. (2003) "Genotyping on a Thermal Gradient DNA Chip," *Genome Res.* 13:467-475.
Kane et al. (1999) "Patterning Proteins and Cells Using Soft Lithography," *Biomaterials* 20:2363-2376.
Kane et al. (Jul. 2006) "Liver-specific functional studies in a microfluidic array of primary mammalian hepatocytes." *Analytical Chemistry* 78(13): 4291-4298.
Karnik et al. (2005) "Electrostatic Control of Ions and Molecules in Nanofluidic Transistors," *Nano Letters* 5(5):943-948.
Karnik et al. (2007) "Rectification of Ionic Current in a Nanofluidic Diode," *Nano Lett.* 7(3):547-551.
Kasianowicz et al. (Nov. 1996) "Characterization of individual polynucleotide molecules using a membrane channel," *Proc. Natl Acad. Sci. USA* 93:13770-13773.
Kasianowicz et al. (Aug. 1, 2006) "Enhancing Molecular Flux Through Nanopores by Means of Attractive Interactions," *Proc. Nat. Acad. Sci. USA* 103(31):11431-11432.

(56) References Cited

OTHER PUBLICATIONS

Kato et al. (Dec. 1991) "AC-Bias Annealing Effects on Radiation-Induced Interface Traps," *IEEE Trans. Nuc. Science.* 38(6):1094-1100.
Katz et al. (2003) "Probing Bimolecular Interactions at Conductive and Semiconductive Surfaces by Impedance Spectroscopy: Routes to Impedimetric Immunosensors, DNA-Sensors, and Enzyme Biosensors," *Electroanalysis* 15(11):913-947.
Ke et al. (Jan. 10, 2007) "Single Step Cell Lysis/PCR Detection of *Escherichia coli* in an Independently Controllable Silicon Microreactor," *Sensors and Actuators B* 120(2):538-544.
Keusgen et al. (2002) "Biosensors: New Approached in Drug Discovery," *Naturwissenschaaften* 89:433-444.
Khademhosseini et al. (2005) "Cell docking inside microwells within reversibly sealed microfluidic channels for fabricating multiphenotype cell arrays." *Lab on a Chip* 5(12): 1380-1386.
Khandurina et al. (Jul. 1, 2000) "Integrated System for Rapid PCR-Based DNA Analysis in Microfluidic Devices," *Anal. Chem.* 72(13):2995-3000.
Kikuchi et al. (1992). "Effects of chronic administration of noradrenaline and glucagon on in vitro brown adipose tissue thermogenesis." *Jpn J Physiol* 42(1): 165-70.
Killander et al. (May 1965) "Quantittative Cytochenical Studies on Interphase Growth: I. Determination of DNA, RNA and Mass Content of Age Determines Mouse Fibroblasts In vitro and of Intercellular Variation in Generation Time," *Exp. Cell Res.* 38(2):272-284.
Kim et al. (Jan. 2006) "Atomic Layer Deposition of Ultrathin Metal-Oxide Films for Nano-Scale Device Applications," *J. Korean Phys. Soc.* 48(1):5-17.
Kim et al. (2006) "Rapid Fabrication of Uniformly Sized Nanopores and Nanopore Arrays for Parallel DNA Analysis," *Adv. Mater.* 18:3149-3153.
Kim et al. (2006). "Live lymphocyte arrays for biosensing." *Advanced Functional Materials* 16(10): 1313-1323.
Kim et al. (2006). "Microfluidic arrays for logarithmically perfused embryonic stem cell culture." *Lab on a Chip* 6(3): 394-406.
Kim et al. (2007) Nanopore sensor for fast label-free detection of short double-stranded DNAs. *Biosensors Bioelectron.* 22:2926-2931.
King et al. (2007) "A high-throughput microfluidic real-time gene expression living cell array." *Lab on a Chip* 7:77-85.
Knoll et al. (Web Release Mar. 20, 2008) "Tethered bimolecular lipid membranes—A novel model membrane platform," *Electrochim. Acta* 53:6680-6689.
Knopfmacher et al. (2010) "Nernst Limit in Dual Gated Si-Nanowire FET Sensors," *Nano Lett..* 10(6):2268-2274.
Kohli et al. (Aug. 13, 2004) "DNA-Functionalized Nanotube Membranes with Single-Base Mismatch Selectivity," *Science* 305:984-986.
Kopp et al. (May 15, 1998) "Chemical Amplification: Continuous-Flow PCR on a Chip," *Science* 280:1046-1048.
Kowalczyk et al. (Jul. 2011) "Single-molecule transport across an individual biomimetic nuclear pore complex," *Nat. Nanotechnol.* 6:433-438.
Kruise et al. (Jan. 1992) "Detection of Charged Proteins by Means of Impedance Measurements," *Sens. Actu. B* 6(1-3):101-105.
Kubitsch, H.E. (1970) "Evidence for the Generality of Linear Cell Growth," *J. Theor. Biol.* 28:15-29.
Kulski et al. (Mar. 1995) "Use of a Multiplex PCR to Detect and Identify *Mycobacterium avium* and *M. Intracellulare* in Blood Culture Fluids of AIDS Patients," *J. Clin. Microbiol.* 33(3):668-674.
Lagally et al. (Web Release Jan. 3, 2001) "Single-Molecule DNA Amplification and Analysis in an Integrated Microfluidic Device," *Anal. Chem.* 73(3):565-570.
Lagerqvist et al. (2006) Fast DNA Sequencing via Transverse Electronic Transport. *Nano Lett.* 6(4):779-782.
Laird, P.W. (Apr. 2003) "The power and the promise of DNA methylation markers," *Nat. Rev. Cancer* 3:253-266.

Langford et al. (2011) "Unsupported planar lipid membranes formed from mycolic acids of *Mycobacterium tuberculosis*," *J. Lipid Res.* 52:272-277.
Lee et al. (Nov. 3, 2003) "Dielectrophoresis and Electrohydrodynamics-Mediated Fluidic Assembly of Silicon Resistors," *Appl. Phys. Lett.* 83(18):3833-3835.
Lee et al. (1997) CG island methylation changes near the GSTP1 gene in prostatic carcinoma cells detected using the polymerase chain reaction: A new prostate cancer biomarker. *Cancer Epidem. Biomar.* 6:443-450.
Lee et al. (2006). "Nanoliter scale microbioreactor array for quantitative cell biology." *Biotechnology and Bioengineering* 94(1): 5-14.
Lee et al. (2008) "Electrical Detection of Biological Interaction Between TAT Peptide and TAR RNA via GaAs Junction Field Effect Transistors," *J. Phys. Chem.* 103(11):114510.
Lee et al. (Apr.1 1999) "Effects of Buried Oxide on Electrical Performance of Thin-Film Silicon-on-Insulator Metal-Oxide-Semiconductor Field-Effect Transistor," *J. Appl. Phys.* 85(7):3912-3915.
Lee et al. (Mar. 1 2002) "Protein Nanoarrays Generated by Dip-Pen Nanolithography," *Science* 295:1702-1705.
Lehmann et al. (Jun. 2000) "Non-Invasive Measurement of Cell Membrane Associated Proton Gradients by Ion Sensitive Field Effect Transistor Arrays for Microphysiological and Bioelectronical Applications," *Biosensors & Bioelectronics* 15(3-4):117-124.
Leporatti et al. (Feb. 4, 2009) "Cytomechanical and Topological Investigatioon of MCF-7 Cells by Scanning Force Microscopy," *Nanotechnology* 20(5):055103.
Li et al. (Jul. 12, 2001) "Ion-beam sculpting at nanometre length scales," *Nature* 412:166-169.
Li et al. (2002) "Dielectrophoretic Separation and Manipulation of Live and Heat-Treated Cells of Listeria on Microfabricated Devices with Interdigitated Electrodes," *Sens. Actuators B* 86:215-221.
Li et al. (Sep. 2003) "DNA molecules and configurations in a solid-state nanopore microscope," *Nat. Mater.* 2:611-615.
Li et al. (Web Release Jan. 28, 2007) "Ultra-sensitive NEMS-based cantilevers for sensing, scanned probe and very high-frequency applications." *Nat Nanotechnol* 2(2): 114-120.
Li et al. (Jun. 5, 2009) "Large-Area Synthesis of High-Quality and Uniform Graphene Films on Copper Foils," *Science* 324:1312-1314.
Li et al. (Feb. 2005) "Characterization and Modeling of a Microfluidic Dielectrophoresis Filter for Biological Species," *J. Microelectromech. Syst.* 14(1):103-112.
Li et al. (Web Release Jan. 8, 2004) "Sequence-Specific Label Free DNA Sensors Based on Silicon Nanowires," *Nano Lett.* 4(2):245-247.
Li, M.Q. (1999) "Scanning Probe Microscopy (ATM/AFM) and Applications in Biology," *Appl. Phys. A* 68:255-258.
Li et al. (Web Release Mar. 11, 2005) "Silicon Nanwires for Sequence-Specific DNA Sensing: Device Fabrication and Simulation," *Appl. Phys. A* 80:1257-1263.
Liao et al. (2005) "Micromachined polymerase chain reaction system for multiple DNA amplification of upper respiratory tract infectious diseases," *Biosens. Bioelectron.* 20:1341-1348.
Lieberman et al. (2010) "Processive Replication of Single DNA Molecules in a Nanopore Catalyzed by phi29 DNA Polymerase," *J. Am. Chem. Soc.* 132:17961-17972.
Lin et al. (Nov. 1994) "Dynamic Liquid Crystal Hot Spot Examination of Functional Failures on Production Testers," *Proceedings of the 20th International Symposium for Testing and Failure Analysis*, Nov. 13-18, :81-86.
Liu et al. (2007) "Electrical Detection of Germination of Model *Bacillus anthracis* Spores in Microfluidic Biochips," *Lab Chip.* 7:603-610.
Liu et al. (2008) "Electrical characterization of DNA molecules in solution using impedance measurements," *Appl. Phys. Lett.* 92:143902.
Liu et al. (2008) "Electrical Detection of DNA Molecules," *BMES Bulletin* 32(3):14-15.
Liu et al. (2010) "Translocation of Single-Stranded DNA Through Single-Walled Carbon Nanotubes," *Science* 327:64-67.
Liu et al. (Mar. 14, 1994) "Self-Limiting Oxidation for Fabricating Sub-5 nm Silicon Nanowires," *Appl. Phys. Lett.* 64(11):1383-1385.

(56) References Cited

OTHER PUBLICATIONS

Liu et al. (Oct. 2008) "Label Free Detection of PCR Amplification," *Sensors IEEE* :550-553.
Loken et al. (1984) "Constancy of cell buoyant density for cultured murine cells." *J Cell Physiol* 118(1):22-26.
Lopez-Buedo et al. (1998) "Thermal Testing on Programmable Logic Devices," *Proc. IEEE ISCAS Conf.* 2:240-243.
Lou et al. (1999) "Fluorescence-Based Thermometry: Principles and Applications," *Rev. Anal. Chem.* 18(4):235-284.
Lu et al. (2007) "Hexamethyldisilazane-Mediated Controlled Polymerization of α-Amino Acid N-Carboxyanhydrides," *J. Am. Chem. Soc.* 129:14114-14115.
Lu et al. (Jun. 2005) "MicorRNA Expression Profiles Classify Human Cancers," *Nature* 435:834-838.
Luan et al. (Jun. 2010) "Base-By-Base Ratcheting of Single Stranded DNA through a Solid-State Nanopore," *Phys. Rev. Lett.* 104:238103.
Luthi et al. (2007) "The CASBAH: a searchable database of caspase substrates." *Cell Death Differ* 14(4):641-650.
MacBeth et al. (Sep. 8, 2000) "Printing Proteins as Microarrays for High-Throughput Function Determination," *Science* 289:1760-1763.
Mager et al. (2008) "Nanopore-Spanning Lipid Bilayers for Controlled Chemical Release," *Adv. Mater.* 20:4423-4427.
Manning et al. (2003) "A Versatile Multi-Platform Biochip Surface Attachment Chemistry," *Mater. Sci. Eng. C* 23:347-351.
Mardis, E.R. (2008) "Next-Generation DNA Sequencing Methods," *Annu. Rev. Genom. Human Genet.* 9:387-402.
Margulies et al. (Sep. 15, 2005) "Genome Sequencing in Open Microfabricated High Density Picoliter Reactors," *Nature* 437:376-389.
Mathe et al. (Nov. 2004) "Nanopore Unzipping of Individual DNA Hairpin Molecules," *Biophys. J.* 87:3205-3212.
Maxam et al. (Feb. 1977) "A New Method for Sequencing DNA," *Proc. Nat. Acad. Sci. USA* 74(2):560-564.
McNally et al. (2010) "Optical Recognition of Converted DNA Nucleotides for Single-Molecule DNA Sequencing Using Nanopore Arrays," *Nano Lett.* 10:2237-2244.
Meller et al. (Feb. 1, 2000) "Rapid nanopore discrimination between single polynucleotide molecules," *Proc. Natl Acad. Sci. USA* 97(3):1079-1084.
Meller et al. (2002) "Single molecule measurements of DNA transport through a nanopore," *Electrophoresis* 23:2583-2591.
Merchant et al. (2010) "DNA Translocation through Graphene Nanopores," *Nano Lett.* 10:2915-292.
Merryman et al. (Apr. 2009) "Viscoelastic Properties of the Aortic Valve Interstitial Cell," *J. Biomech. Eng. Trans. Asme* 131:041005.
Metzker, M.L. (Jan. 2010) "Sequencing technologies—the next generation," *Nat. Rev. Genet.* 11:31-46.
Milovic et al. (Sep. 5, 2006) "Monitoring of Heparin and its Low-Molecular-Weight Analogs by Silicon Filed Effect," *Proc. Nat. Acad. Sci. USA* 103(36):13374-13379.
Min et al. (Mar. 2011) "Fast DNA sequencing with a graphene-based nanochannel device," *Nat. Nanotechnol.* 6:162-165.
Mingos et al. (1991) "Tilden Lecture. Applcations of Microwave Dielectric Heating Effects to Synthetic Problems in Chemistry," *Chem. Soc. Rev.* 20:1-47.
Mirsaidov et al. (2009) "Nanoelectromechanics of Methylated DNA in a Synthetic Nanopore," *Biophys. J.* 96:L32-L34.
Mitchell et al. (2008) "Chemical Tags Facilitate the Sensing of Individual DNA Strands with Nanopores13,"*Angew. Chem. Int. Ed.* 47:5565-5568.
Mitchison (2003) "Growth During the Cell Cycle," *Int. Rev. Cyto.* 226:165-258.
Mitchison (Web Release Feb. 9, 2005) "Single Cell Studies of the Cell Cycle and Some Models," *Theor. Biol. Med. Model.* 2:4.
Muller et al. (Jun. 1999) the Electronic Structure at the Atomic Scale of Ultrathin Gate Oxides, *Nature* 399(6738):758-761.
Murphy, L. (2006) "Biosensors and Bioelectrochemistry," *Curr. Opin. Chem. Biol.* 10:177-184.

Nair et al. (2006) "Performance Limits of Nanobiosensors," *Appl. Phys. Lett.* 88(23):233120.
Nair et al. (Dec. 2007) "Design Considerations of Nanowire Biosensors," *IEEE Trans. Electon. Dev.* 54(12):3400-3408.
Nair et al. (Dec. 2007) "Dimensionally Frustrated Diffusion Towards a Fractal Aborber," *Phys. Rev. Lett.* 99:256101.
Nair et al. (Web Release Apr. 3, 2008) "Screening-Limited Response of NanoBiosensors," *Nano Letters* 8(5):1281-1285.
Nakamura et al. (2003) "Current Research Activity in Biosensors," *Anal. Bioanal. Chem.* 377:446-468.
Nam et al. (2009) "Ionic Field Effect Transistors with Sub-10 nm Multiple Nanopores," *Nano Letters* 9(5):2044-2048.
Neff et al. (Oct. 8, 2007) "Label-Free Electrical Determination of Trypsin Activity by a Silicon-on-Insulator Based Thin Film Resistor," *ChemPhysChem* 8(14):2133-2137.
Nelson et al. (2010) "Detection of Nucleic Acids with Graphene Nanopores: Ab Initio Characterization of a Novel Sequencing Device," *Nano Letters* 10:3237-3242.
Neuzil et al. (2006) "Disposable Real-Time Micro-PCR Device: Lab-on-a-Chip at a Low Cost," *Mol. Biostst.* 2:292-298.
Nguyen et al. (1989) "XPS Study of SiO Thin Films and SiO-Metal Interfaces," *J. Phys. Condens Matter* 1:5197-5204.
NHGRI (Mar. 11, 2010) *NIH News Release* "NHGRI Seeks Next Generation of Sequencing Technologies," http://www.genome.gov/12513210.
NHGRI (Aug. 3, 2011) Advanced Sequencing Technology Awards 2008) http://www.genome.gov/27527584.
Nie et al. (2007) "On-chip cell migration assay using microfluidic channels." *Biomaterials* 28(27):4017-4022.
Nikolaides et al. (Apr. 2004) "Characterization of a Silicon-on-Insulator Based Thin Film Resistor in Electrolyte Solutions for Sensor Applications," *J. Appl. Phys.* 95(7):3811-3815.
Nilsson et al. (2006) "Localized Functionalization of Single Nanopores," *Adv. Mater.* 18:427-431.
Noble, R.D. (1991) "Generalized Microscopic Mechanism of Facilitated Transport in Fixed Carrier Membranes," *J. Membr. Sci.* 75:121-129.
Notomi et al. (2000) "Loop-Mediated Isothermal Amplification of DNA," *Nuc. Acids. Res.* 28(12):E63.
Nugaeva et al. (2005). "Micromechanical cantilever array sensors for selective fungal immobilization and fast growth detection." *Biosensors & Bioelectronics* 21(6): 849-856.
Nunez et al. (1999) "Long-Range Oxidative Damage to DNA: Effects of Distance and Sequence," *Chem. Biol.* 6:85-97.
Olasagasti et al. (Nov. 2010) "Replication of individual DNA molecules under electronic control using a protein nanopore," *Nat. Nanotechnol.* 5:798-806.
Olie et al. (Aug. 17, 1998) "Apparent caspase independence of programmed cell death in *Dictyostelium*." *Curr Biol.* 8(17): 955-958.
Olthuis et al. (1994) "Characterization of Proteins by Means of their Buffer Capacity, Measureed with an ISFET-Based Coulometric Sensor—Actuator System," *Biosensors & Bioelectronics* 9(9-10):743-751.
Omura et al. (1977) "A new alkaloid AM-2282 OF *Streptomyces* origin. Taxonomy, fermentation, isolation and preliminary characterization", *J. Antibiot.*, 30(4):275-282.
Pandana et al. (Jun. 2008) "A Versatile Bimolecular Charge-Based Sensor Using Oxide-Gated Carbon Nanotube Transistor Arrays," *IEEE SEns. J.* 8(6):655-.
Park et al (Web Release Sep. 26, 2007) "Selective Surface Functionalization of Silicon Nanowires via Nanoscale Joule Heating," *Nano Lett.* 7(10):3106-3111.
Park et al. (2007) "Selective Functionalization of Silicon Micro/Nanowire Sensors via Localized Joule Heating," *IEEE-NEMS* 2:899-904.
Park et al. (2007) "Electrical capture and lysis of vaccinia virus particles using silicon nano-scale probe array." *Biomed Microdevices* 9(6): 877-878.
Park et al. (2008) "Living cantilever arrays for characterization of mass of single live cells in fluids", *Lab Chip* 8:1034-1041.
Park et al. (2009) "MEMS-based resonant sensor with uniform mass sensitivity", Digest Tech. Papers, Transducers '09 Conference, Denver, Colorado, Jun. 21-25, pp. 1956-1958; W3P.052.

(56) References Cited

OTHER PUBLICATIONS

Park et al. (2009) "MEMS-based resonant sensor with uniform mass sensitivity," Poster Presented at The 15th International Conference on Solid-State Sensors, Actuators and Microsystems. Denver, Colorado, Jun. 21-25.
Park et al. (Nov. 302010) "Measurement of Adherent Cell Mass and Growth," Proc. Nat. Acad. Sci. USA 107(48):20691-20696.
Park et al. (Jun. 2011) "MEMS Mass Sensors with Uniform Sensitivity for Monitoring Cellular Apoptosis," *16th International Solid-State Sensors, Actuators and Microsystems Conference (TRANSDUCERS)* pp. 759-762; M4c.003.
Patalsky et al. (Sep. 28, 2004) "Electrical Detection of Single Viruses," *Proc. Nat. Acad. Sci. USA* 101(39):14017-14022.
Patolsky et al. (Apr. 2005) "Nanowire Nanosensors," *Mat. Today* :20-28.
Patolsky et al. (Aug. 25, 2006) "Detection, Stimulation, and Inhibition of Neuronal Signals with High-Density Nanowire Transistor Arrays," *Science* 313(5790):1100-1104.
Patolsky et al. (Web Release Jul. 1, 2006) "Nanowire-Based Biosensors," *Anal. Chem.* 78(13):4260-4269.
Patolsky et al. (Web Release Nov. 16, 2006) "Fabrication of Silicon Nanowire Devices for Ultrasensitive, Label-Free, Real-Time Detection of Biological and Chemical Species," *Nature Protocols* 1(4):1711-1724.
Peterson et al. (Web Release Mar. 10, 2009) "PAC-1 activates procaspase-3 in vitro through relief of zinc-mediated inhibition." *J Mol Biol* 388(1): 144-58.
Platt et al. (Jul. 2007) "Improved DNA Sequencing Quality and Efficienct Using an Optimized Fast Cycle Sequence Protocol," *Biotechniques* 43:58-62.
Popescu et al. (Aug. 2008) "Optimal Imaging of Cell Mass and Growth Dynamics," *Am J Physiol Cell Physiol* 295(2):C538-0544.
Postma, H.W.C. (Web Release Jan. 4, 2010) "Rapid Sequencing of Individual DNA Molecules in Graphene Nanogaps," *Nano Lett.* 10:420-425.
Pourmand et al. (Apr. 25, 2006) "Direct Electrical Detection of DNA Synthesis," *Proc. Nat. Acad. Sci. USA* 103(17):6466-6470.
Power et al. (Apr. 14, 2004) "Refractive Index at Infrared Wavelengths and Dielectric Permittivity of Pure and Fluorinated Silicon Dioxide from Measurements of their Thin Fims Deposited on Si," *J. Phys. D. Appl. Phys.* 37:1362-1370.
Prasongkit et al. (Apr. 15, 2011) "Transverse Conductance of DNA Nucleotides in a Graphene Nanogap from First Principles," *Nano Lett.* 11:1941-1945.
Prescesky et al. (1992) "Silicon Micromachining Technology for Subnanogram Discrete Mass Resonant Biosensors." *Canadian Journal of Physics* 70(10-11): 1178-1183.
Prins et al. (1999) "Thermal Oxidation of Silicon-on-Insulator Dots," *Nanotechnology* 10:132-134.
Rashidian et al. (1993) "Electrothermal Microactuators Based on Dielectric Loss Heating," *IEEE* :24-29.
Reddy et al. (Web Release Jan. 4, 2011) "High-k Dielectric $Al_2O_3$ Nanowire and Nanoplate Field Effect Sensor for Improved pH Sensing," *Biomed. Microdev.* 13:335-344.
Rhee et al. (Web Release Oct. 19, 2006) "Nanopore sequencing technology: research trends and applications," *Trends Biotechnol.* 24(12):580-586.
Rincon-Restrepo et al. (Jan. 11, 2011) "Controlled Translocation of Individual DNA Molecules through Protein Nanopores with Engineered Molecular Brakes," *Nano Lett.* 11:746-750.
Robertson, J. ( Dec. 2004) "High Dielectric Constant Oxides," *European Physical Journal-Applied Physics* 28(3):265-291.
Rodriguez et al. (Jui. 19, 2005) "A Microchip CD4 Counting Method for HIV Monitoring in Resource-Poor Settings, " *PLoS Med* 2(7):e182.
Roitman et al. (Oct. 1998) "Electrical Detection of Defects in SIMOX Buried Oxides: Pipes and Precipitates," *Proceedings 1998 IRRR International SOI Conference* :167-168.
Ronaghi et al. (Jul. 17, 1998) "A Sequencing Method Based on Real-Time Pyrophosphate," *Science* 281:363-365.
Ross et al. (Web Release Jul. 24, 2001) "Temperature Measurement in Microfluidic Systems Using a Temperature-Dependent Fluorescent Dye," *Anal. Chem.* 73(17):4117-4123.
Sader, J. E. (Jul. 1, 1998) "Frequency response of cantilever beams immersed in viscous fluids with applications to the atomic force microscope." *Journal of Applied Physics* 84(1): 64-76.
Sagiv, J. (Jan. 2, 1980) "Organized Monolayers by Adsorption. 1. Formation and Structure of Oleophobic Mixed Monolayers on Solid Surfaces," *J. Am. Chem. Soc.* 102(1):92-98.
Salisbury et al. (1984) "Nanometer scale electron beam lithography in inorganic materials," *Appl. Phys. Lett.* 45:1289-1291.
Sanger et al. (Dec. 1977) "DNA Sequencing with Chain-Terminating Inhibitors," *Proc. Nat. Acad. Sci. USA* 74(12):5463-5467.
SantaLucia, Jr. John (Feb. 1998) "A Unified View of Polymer, Dumbell, and Oligonucleoride DNA Nearest-Neighbor Thermodynamics," *Proc. Nat. Acad. Sci. USA* 95:1460-1465.
Sakata et al. (2006) "DNA Sequencing Based on Intrinsic Molecular Charges," *Angew. Chem. Int. Ed.* 45:2225-2228.
Schasfoort et al. (1989) "Modulation of the ISFET Response by an Immunological Reaction," *J. Sensors and Actuators* 17(3-4):531-535.
Scherer et al. (2009) "Poly-N-acetyl glucosamine nanofibers: a new bioactive material to enhance diabetic wound healing by cell migration and angiogenesis." *Ann Surg* 250(2): 322-30.
Schneider et al. (2010) "DNA Translocation through Graphene Nanopores," *Nano Lett.* 10:3163-3167.
Schowalter et al. (2007) "Efficient Isothermal Amplification of the Entire Genome from Single Cells," *Methods Mol. Med.* 132:87-99.
Service, R.F. (Mar. 17, 2006) "Gene Sequencing: The Race for the $1000 Genome," *Science* 311:1544-1546.
Shah et al. (Oct. 31, 2007) "Microwave Dielectric Heating of Fluids in an Integrated Microfluidic Device," *J. Micromech. Microeng.* 17(11):2224-2230.
Sheehan et al. (2005) "Detection Limits for Nanoscale Biosensors," *Nanoletters* 5(4):803-807.
Shi et al. (Mar. 25, 1993) "Rheological Properties of Mammalian Cell Culture Suspensions: Hybridoma and HeLa Cell Lines," *Biotechnol. Bioeng.* 41(7):745-754.
Shroff et al. (1995) "Dynamic Micromechanical Properties of Cultures Rat Atrial Myocytes Measured by Atomic Force Microscopy," *Am. J. Physiol. Cell Physiol.* 38:C286-C292.
Sigalov et al. (2007) "Detection of DNA Sequences Using an Alternating Electric Field in a Nanopore Capacitor," *Nano Lett.* 8(1):56-63.
Sin et al. (2008) "Scaling Analysis of a Universal Electrode for Molecular Biosensors," 3rd IEEE International Conference on Nano/Micro Engineered and Molecular Systems, *IEEE NEMS* pp. 1151-1155.
Singer et al. (2010) "Nanopore Based Sequence Specific Detection of Duplex DNA for Genomic Profiling," *Nano Lett.* 10:738-742.
Singh et al. (2006) "PCR Thermal Management in an Integrated Lab on a Chip," *J. Phys. Conf. Series* 34:222-227.
Situma et al. (Web Release Dec. 20, 2006) "Imobilized Molecular Beacons: A New Strategy Using UV-Activated Poly(methyl methacrylate) Surfaces to Provide Large Fluorescence Sensitivities for Reporting on Molecular Association Events," *Anal. Biochem.* 363:35-45.
Siwy et al. (2005) "Protein Biosensors Based on Biofunctionalized Conical Gold Nanotubes," *J. Am. Chem. Soc.* 127:5000-5001.
Siwy et al. (Web Releace Dec. 4, 2009) "Engineered voltage-responsive nanopores," *Chem. Soc. Rev.* 39:1115-1132.
Smeets et al. (2006) "Salt Dependence of Iron Transport and DNA Translocation through Solid-State Nanopores," *Nano Lett.* 6(1):89-95.
Song et al. (May 23, 2011) "Atomic-Scale Electron-Beam Sculpting of Near-Defect-Free Graphene," *Nanostructures. Nano Lett.* 11:2247-2250.
Soper et al. (2006) "Point-of-Care Biosensor Systems for Cancer Diagnostic/Prognostics," *Biosensors Bioelectronics* 21:1932-1942.
Squires et al. (2004) "Induced—Charge Electro-Osmosis," *J. Fluid Mech.* 509:217-252.

(56) References Cited

OTHER PUBLICATIONS

Squires et al. (Web Release Apr. 7, 2008) "Making it Stick: Convection, Reaction and Diffusion in Surface-Based Biosensors," *Nature Biotechnology* 26(4):417-426.
Stahlbush et al. (Dec. 1995) "Bulk Trap Formation by High Temperature Annealing of Buried Thermal Oxides," *IEEE Trans. Nuc. Sci.* 42(6):1708-1716.
Star et al. (Jan. 24, 2006) "Label-Free Detection of DNA Hybridization Using Carbon Nanotube Network Field-Effect Transistors," *Proc. Nat. Acad. Sci. USA* 103(4):921-926.
Stein et al. (Jul. 2004) "Surface-Charge-Governed Ion Transport in Nanofluidic Channels," *Physical Review Letters* 93(3):035901.
Steitz, T.A. (Jun 18, 1999) "DNA Polymerase Structural Diversity an Common Mechanisms," *J. Biol. Chem.* 274(25):17395-17398.
Stern et al. (Feb. 1, 2007) "Label-Free Immunodetection with CMOS-Compatible Semiconducting Nanowires," *Nature* 445:519-522.
Stern et al. (Web Release Dec. 13, 2009) "Label-Free Biomarker Detection from White Blood," *Nature Nanotechnology* 5(2):138-142.
Stern et al. (Web Release Oct. 3, 2007) "Importance of the Debye Screening Length on Nanowire Field Effect Transistor Sensors," *Nano Letters* 7(11):3405-3409.
Stern et al. (Web Release Sep. 3, 2008) "Label-Free Electronic Detection of the Antigen-Specific T-Cell Immune Response," *Nano Letters* 8(10):3310-3314.
Stoddart et al. (May 12, 2009) "Single-nucleotide discrimination in immobilized DNA oligonucleotides with a biological nanopore," *Proc. Natl Acad. Sci. USA* 106(19):7702-7707.
Storm et al. (Aug. 2003) "Fabrication of solid-state nanopores with single nanometer precision," *Nat. Mater.* 2:537-540.
Storm et al. (Jul. 2005) "Fast DNA Translocation through a Solid-State Nanopore," *Nano Lett.* 5(7):1193-1197.
Storm et al. (May 6, 2005) "Translocation of double-strand DNA through a silicon oxide nanopore," *Phys. Rev. E* 71:051903.
Strathdee et al. (2002) "Aberrant DNA methylation in cancer: potential clinical interventions," *Expert Rev. Mol. Med.* 4:1-17.
Taff et al. (2005). "A scalable addressable positive-dielectrophoretic cell-sorting array." *Analytical Chemistry* 77(24): 7976-7983.
Tanaka et al. (Aug. 2009) "Partial sequencing of a single DNA molecule with a scanning tunnelling microscope," *Nat. Nanotechnol.* 4:518-522.
Taniguchi et al. (2009) "Fabrication of the gating nanopore device," *AppL Phys. Lett.* 95:123701-123703.
Taylor et al. (1978) "Chemical Reactions of N+2 Ion Beams with Group IV Elements and Their Oxides," *J. Electron Spectrosc. Relat. Phenom.* 13:435-444.
Taylor et al. (Aug. 1, 1997) "Optimization of the Performance of the Polymerase Chain Reaction in Silicon-Based Microstructures," *Nucleic Acids Res.* 25(15):3164-3168.
Taylor et al. (Feb. 15, 1978) "Interactions of Ion Beams with Surfaces. Reactions of Nitrogen with Siliconand its Oxides," *J. Chem. Phys.* 68(4):1776-1784.
The International HapMap, (Oct. 27, 2005) C. A haplotype map of the human genome. *Nature* 437, 1299-1320.
Thomas et al. (Oct. 26, 2004) "Coding single-nucleotide polymorphisms associated with complex vs. Mendelian disease: Evolutionary evidence for differences in molecular effects," *Proc. Natl Acad. Sci. USA* 101(43):15398-15403.
Thompson et al. (2004) "Dynamic Gene Expression Profiling Using a Microfabricated Living Cell Array," *Anal. Chem.* 76(14):4098-4103.
Thundat et al. (Mar. 27, 1995) "Detection of mercury vapor using resonating microcantilevers", *Appl. Phys. Lett.* 66(13):1695-1699.
Timmer et al. (2007) "Caspase Substrates," *Cell Death Differ* 14(1):66-72.
Tong et al. (Web Release Jan. 29, 2009) "Novel Top-Down Wafer-Scale Fabrication of Single Crystal Silicon Nanowires," *Nano Letters* 9(3):1015-1022.

Tsuda et al. (Web Release Aug. 20, 2007) "Cellular Control of Tissue Architectures using a Three-Dimensional Tissue Fabrication Technique," *Biomaterials* 28(33):4939-4946.
Tsutsui et al. (Apr. 2010) "Identifying single nucleotides by tunnelling current," *Nat. Nanotechnol.* 5:286-290.
Tyagi et al. (Mar. 1996) "Molecular Beacons: Probes that Fluoresce Upon Hybridization," *Nat. Biotechnol.* 14:303-308.
Tzur et al. (Jul. 10, 2009) "Cell Growth and Size Homeostasis in Proliferating Animal Cells," *Science* 325(5937):167-171.
Van kerkhof et al. (1993) "Development of an ISFET Based Heparin Densor Using the Ion-Step Measuring Method," *Biosensors & Bioelectronics* 8(9-10):463-472.
Vanderschoot et al. (1987) "ISFET Based Enzyme Sensors," *Biosensors* 3(3):161-186.
Vanderschoot et al. (1987) "The pH-Static Enzyme Sensor: An ISFET-Based Enzyme Sensor, Insensitive to the Buffer Capacity of the Sample," *Analytica Chimica Acta* 199:157-160.
van Hal (Mar. 1995) "A Novel Description of ISFET Sensitivity with the Buffer Capacity and Double-Layer Capacitance as Key Parameters," *Sens. Actu. B Chem.* 24(1-3):201-205.
van Hal et al. (1996) "A General Model to Describe the Electrostatic Potential at Electrolyte Oxide Interfaces," *Adv. Colloid Interface Sci.* 69(1-3):31-62.
Venkatesan et al. (2009) "Highly Sensitive, Mechanically Stable Nanopore Sensors for DNA Analysis," *Adv. Mater.* 21(27):2771-2776.
Venkatesan et al. (2010) "DNA Sensing Using Nanocrystalline Surface-Enhanced Al2O3 Nanopore Sensors," *Adv. Funct. Mater.* 20:1266-1275.
Venkatesan et al. (2011) "Lipid bilayer coated AI2O3 nanopore sensors: towards a hybrid biological solid-state nanopore," *Biomed. Microdevices* 13:671-682.
Venkatesan et al. (Aug. 2011) "Nano-fabricated Graphene-AI2O3 Nanopores and Nanopore arrays for the Sensitive Detection of DNA and DNA-Protein Complexes", Proceeding of the 2011 Manufacturing Technologies 2011 Workshop Aug. 8-10, 2011 Napa, California, USA.
Venkatesan et al. (Web Release Sep. 18, 2011) "Nanopore Sensors for Nucleic Acid Analysis," *Nat. Nanotechnol.* 6:615-624.
Venkatesan et al. (2011) "Solid-State Nanopore Sensors for Nucleic Acid Analysis," Iqbal et al. eds., In; *Nanopores: Sensing and Fundamental Biological Interactions*, Ed. 1, Springer, New York.
Vercoutere et al. (Mar. 2001) "Rapid discrimination among individual DNA hairpin molecules at single-nucleotide resolution using an ion channel," *Nat. Biotech.* 19:248-252.
Vercoutere et al. (2003) "Discrimination Among Individual Watson-Crick Base Pairs at the Termini of Single DNA Hairpin Molecules," *Nuc. Acids Res.* 31(4):1311-1318.
Voinova et al. (Oct. 2002) "Missing Mass' Effect in Biosensor's QCM Applications," *Biosens. Bioelectron.* 17(10):835-841.
Volinia et al. (Feb. 14, 2006) "A microRNA expression signature of human solid tumors defines cancer gene targets," *Proc. Natl Acad. Sci. USA* 103(7):2257-2261.
Waggoner et al. (Web Release Jul. 25, 2007) "Micro-and nanomechanical sensors for environmental, chemical, and biological detection," *Lab Chip* 7:1238-1255.
Wang et al. (Web Release Dec. 5, 2005) "A disposable microfluidic cassette for DNA amplification and detection," *Lab Chip* 6(1):46-53.
Wang et al. (2006) "Electrochemical Biosensors: Towards Point-of-Care Cancer Diagnostics," *Biosensors Bioelectronics* 21:1887-1892.
Wang et al. (Mar. 1, 2005) "Label-Free Detection of Small-Molecule-Protein Interactions by Using Nanowire Nanosensors," *Proc. Nat. Acad. Sci. USA* 102(9):3208-3212.
Wanunu et al. (2007) "Chemically Modified Solid-State Nanopores," *Nano Lett.* 7(6):1580-1585.
Wanunu et al. (Nov. 2008) "DNA Translocation Governed by Interactions with Solid-State," *Nanopores. Biophys. J.* 95:4716-4725.
Wanunu et al. (2010) "Discrimination of Methylcytosine from Hydroxymethylcytosine in DNA Molecules," *J. Am. Chem. Soc.* 133:486-492.
Wanunu et al. (Feb. 2010) "Electrostatic focusing of unlabelled DNA into nanoscale pores using a salt gradient," *Nat. Nanotechnol.* 5:160-165.

(56) References Cited

OTHER PUBLICATIONS

Wanunu et al. (Nov. 2010) "Rapid electronic detection of probe-specific microRNAs using thin nanopore sensors," *Nat. Nanotechnol.* 5:807-814.

Waters et al. (Dec. 15, 1998) "Multiple Sample PCR Amplification and Electrophoretic Analysis on a Microchip," *Anal. Chem.* 70:5172-5176.

Weiss et al. (Aug. 1, 1997) "A Coalescent Approach to the Polymerase Chain Reactions: Mathimatical Modeling and Experimental Verification," *Comp. Biol. Chem.* 28:195-209.

Wells, J. (Sep. 30, 2002) "Does Size Matter," *Cell Biol.* 158(7):1156-1159.

Wendell et al. (Nov. 2009) "Translocation of double-stranded DNA through membrane-adapted phi29 motor protein nanopores," *Nat. Nanotechnol.* 4:765-772.

White et al. (2006) "Ionic conductivity of the aqueous layer separating a lipid bilayer membrane and a glass support," *Langmuir* 22:10777-10783.

Wilson et al. (Web Release Apr. 20, 2007) "Integration of Functional Myotubes with a Bio-MEMS device for Non-Invasive Interrogation," *Lab Chip* 7(7):920-922.

Woolley et al. (Dec. 1996) "Functional Integration of PCR Amplification and Capillary Electrophoresis in a Microfabricated DNA Analysis Device," *Anal. Chem.* 68(23):4081-4086.

Yamamoto et al. (2002) "Phospholipids Promote Dissociation of ADP from the *Mycobacterium avium* DnaA Protein," *J. Biochem.* 131(2):219-224.

Yan et al. (2006) "Towards Rapid DNA Sequencing: Detecting Single-Stranded DNA with a Solid-State Nanopore," *Small* 2(3):310-312.

Yang et al. (2006) "A Mulitifunctional Micro-Fluidic System for Dielectrophoretic Concentration Coupled with Immuno-Capture of Low Numbers of *Listeria Monocytogenes*," *Lab Chip*, 6:896-905.

Yang et al. (Apr. 2006) "Zeptogram-Scale Nanomechanical Mass Sensing," *Nano Lett.* 6(4):583-586.

Yang et al. (Dec. 20, 2005) "Conductivity and pH Dual Detection of Growth Profile of Healthy and Stressed *Listeria monocytogenes*," *Biotechnol. Bioeng.* 92(6):685-694.

Yi et al. (Jan. 15, 2005) "Theretical and Experimental Study Towards a Nanogap Dielectric Biosensor," *Biosens. Bioelectron.* 20(7):1320-1326.

Yin et al. (Web Release Jul. 20, 2006) "Electric Heating Effects in Nematic Liquid Crystals," *J. Appl. Phys.* 100(2):024906.

Yoon et al. (2002) "Precise Temperature Control and Rapid Thermal Cycling in a Micromachined DNA Polymerase Chain Reaction Chip," *J. Micromech. Microeng.* 12:813-823.

Yu et al. (2005) "Biosensors in Drug Discovery and Drug Analysis," *Anal. Lett.* 38:1687-1701.

Yusko et al. (Apr. 2011) "Controlling protein translocation through nanopores with bio-inspired fluid walls," *Nat. Nanotechnol.* 6:253-260.

Zetterberg et al. (Aug. 1965) "Quantitative Cyclochemical Studies on Interphase Growth: II. Derivation of Synthesis Curves from the Distribution of DNA, RNA and Mass Values of Individual Mouse Bifroblasts in Vitro," *Exp. Cell Res.* 39(1):22-32.

Zhang et al. (Nov. 5. 2001) "Electric-Field-Directed Growth of Aligned Single-Walled Carbon Nanotubes,"*Appl. Phys. Lett.* 79(19):3155-3157.

Zhang et al. (2006) "Electrical Conductivity in Silicon Nanomembranes," *New J. Phys.* 8:1-19.

Zhang et al. (Web Release Jun. 18, 2007) "Miniaturized PCR Chips for Nucleic Acid Amplification and Analysis: Latest Advances and Future Trends," *Nuc. Acids Res.* 35(13):4223-4237.

Zhang et al. (Jul. 17, 2009) "RIP3, an Energy Metabolism Regulator that Switches TNF-Induced Cell Death from Apoptosis to Necrosis," *Science* 325(5938):332-336.

Zhang et al. (Apr. 15, 2009) "Label-Free Direct Detection of MiRNAs with Silicon Nanowire Biosensors," *Biosensors & Bioelectronics* 24(8):2504-2508.

Zhang et al. (Feb. 9, 2006) "Electronic Transport in Nanometre-Scale Silicon-on-Insulator Membranes," *Nature* 439:703-706.

Zhang et al. (Jun. 15, 2008) "Highly Sensitive Measurements of PNA-DNA Hybridization Using Oxide-Etched Silicon Nanowire Biosensors," *Biosensors & Bioelectronics* 23(11):1701-1707.

Zhang et al. (Web Release Mar. 1, 2008) "DNA Sensing by Silicon Nanowire: Charge Layer Distance Dependence," *Nano Letters* 8(4):1066-1070.

Zhao et al. (2007) "Detecting SNPs Using a Synthetic Nanopore," *Nano Lett.* 7(6):1680-1685.

Zheng et al. (Web Release Sep. 18, 2005) "Multiplexed Electrical Detection of Cancer Markers with Nanowire Sensor Arrays," *Nature Biotechnology* 23(10):1294-1301.

Zhu et al. (Web Release Mar. 19, 2009) "Silicon Nanowire NVM with High-k Gate Dielectric Stack," *Microelectron. Eng.* 86(7-9):1957-1960.

Zvanut et al. (May 1, 1995) "Generation of Thermally Induced Defects in Buried SiO2 Films," *J. AppL Phys.* 77(9):4329-4333.

Zwolak et al. (2008) "Colloquium: Physical approaches to DNA sequencing and detection," *Rev. Mod. Phys.* 80:141-165.

* cited by examiner

315

315

418
419
417

420
418

421
418

DNA SEQUENCING AND AMPLIFICATION SYSTEMS USING NANOSCALE FIELD EFFECT SENSOR ARRAYS

CROSS REFERENCE TO RELATED APPLICATION

This application claims the benefit of and priority to PCT International Application PCT/US2009/058739, filed Sep. 29, 2009, and U.S. Provisional Application 61/101,062 filed on Sep. 29, 2008, the disclosures of which are hereby incorporated by reference in their entirety.

STATEMENT REGARDING FEDERALLY SPONSORED RESEARCH OR DEVELOPMENT

This invention was made with United States governmental support under Award No. ECS 0554990 awarded by the National Science Foundation and Award No. 1 R21 EB006308-01 awarded by the National Institutes of Health. The U.S. government has certain rights in the invention.

BACKGROUND OF THE INVENTION

This invention is in the field of chemical and biological sensing and biotechnology. This invention relates generally devices and methods useful for amplification and/or sensitive detection of molecules, for example nucleic acids.

Recent advances in nanotechnology and integration of top-down and bottom-up fabrication techniques have enabled the realization of integrated devices with nano-scale sensors for the direct, label-free, and electronic detection of biomolecules. These advances are moving towards the vision of personalized and quantitative molecular medicine. Many disease states and disorders in medicine can be attributed to the aberrations and defects in the DNA molecule of individuals. Hence, sequencing the DNA molecule and sequencing of the entire genome in a cost effective, accurate and rapid manner is desirable.

One of the most promising methods being commercialized is the method of 'sequencing by synthesis' where optical detection of each nucleotide added to an existing DNA template molecule that is being polymerized, can be used to obtain the sequence of the starting template.

Recently, the entire genome of a human being, James Watson, was completed within two months by the DNA sequencing company 454 Life Sciences using a novel DNA sequencing approach wherein microfabricated high-density picoliter reactors were used to perform sequencing by synthesis. This method still costs about $1 million, well above the $1,000 per genome target of the National Human Genome Research Institute. Various factors determine the current cost structure of the genome sequence technologies.

The current 'sequence by synthesis' approaches consist of the following major components: (i) the original target molecule to be sequenced is digested into smaller fragments, (ii) each smaller fragment is amplified by 30 to 40 cycle PCR to increase their number to have a high signal/noise ratio for detection at a later step, (iii) synthesis of the complementary strands is performed and the addition of each nucleotide is detected using either an optical fluorescence signal generation or conversion of pyrophosphates (PPi) released during DNA polymerization into a chemiluminescence signal (pyrosequencing) with minimum photon count of 10000 from approximately 10 million conjugations, (iv) the information obtained from each original strand (or amplified strands of the same type) is pieced back together (assembly) using sophisticated software and algorithms to obtain the sequence of the original molecule.

Sequencing approaches based on micro to nanoscale technological developments are able to improve sequencing speed and read accuracy as well as reduce costs of sequencing. Wider application of genomics in medicine, from personalized medicine to point-of-care advanced diagnostic and predictive genomic tools, could one day be achieved if such advances reduce the cost of genome sequencing to the $1000 target of the National Human Genome Research Institute.

A variety of microscale sensor devices have been developed for label-free detection of DNA. For example, U.S. Patent Application Publication No. 2006/0197118 discloses an extended gate field effect transistor sensor device. Probe molecules are immobilized on an exposed metal sensor electrode for detection of target molecules, e.g., DNA, to produce a change in an electrical characteristic of the field effect transistor.

U.S. Patent No. 7,385,267 also discloses a field effect sensor device including a functionalized silicon nanowire serving as a gate electrode for the field effect device. The surfaces of the nanowires are selectively functionalized with reactive binding partners, e.g., for probing DNA molecules.

U.S. Patent Application Publication No. 2007/0292855 discloses a device for electrical detection of molecular binding between a probe molecule and a target molecule. Several independently addressable electrodes positioned above the device serve to attract and trap charged molecules above a channel of the device.

U.S. Patent No. 6,203,683 discloses a device for analysis of polyelectrolytes, such as DNA, which includes electrodes for transporting molecules by dielectrophoresis and a trapping electrode attached to a heating element for heating trapped molecules, for example for thermocycling reactions.

SUMMARY OF THE INVENTION

In one aspect, described herein are field effect chemical sensor devices useful for chemical and/or biochemical sensing. Also provided herein are methods for single molecule detection. In another aspect, described herein are methods useful for amplification of target molecules by PCR.

According to one aspect, a chemical sensor device comprises a semiconductor field effect sensor or transistor having a source, a drain, a gate and a sensing region, wherein the sensing region is positioned between the source and drain and the gate is positioned at least partially below the sensing region, the source, and the drain. For some embodiments, a chemical sensor device is a FIN-FET, a double gate SOI FET, a metal gate FET, an extended gate FET, a strained semiconductor FET or another field effect transistor device.

In some embodiments the semiconductor field effect sensor comprises a semiconductor selected from the group consisting of: Si, Ge, C, any III-V semiconductor, any II-VI semiconductor, and any combination of these materials. In one embodiment, the gate comprises a semiconductor substrate or an electrical contact under a buried oxide. Useful field effect sensors include, but are not limited to: Schottky field effect sensors, field effect sensors fabricated using a top down method and field effect sensors fabricated using a bottom up method, such as nanowires, nanotubes and other nanostructures. The chemical sensor devices may also comprise a gate electrode located below the semiconductor field effect sensor. For some embodiments the source and drain each comprise doped semiconductor, for example, a semiconductor having dopants selected from the group consisting of phosphorus, nitrogen, boron, aluminum, arsenic, antimony, carbon, oxygen and any combination of these. The sensing region for some embodiments comprises a conductive structure commonly referred to as a nanowire or a nanoplate.

In an embodiment, a chemical sensor device comprises one or more voltage controllers electrically connected to the field effect sensor or other components. In one example, a chemical sensor device comprises an AC voltage controller electrically connected to the gate and the source and drain for providing a preselected AC voltage between the gate and the source and/or drain. In another embodiment, a chemical sensor device comprises a DC voltage controller electrically connected to the electrostatic lens electrode and the gate for providing a preselected DC voltage between the electrostatic lens electrode and the gate.

In a specific embodiment, a chemical sensor device comprises an electrostatic lens electrode positioned over the semiconductor field effect sensor. For some embodiments, a distance between the electrostatic lens electrode and the semiconductor field effect sensor is selected from 0.01 to 5 µm, for example 0.5 µm; for other embodiments the electrostatic lens electrode is positioned adjacent to the semiconductor field effect sensor. Useful electrostatic lenses include lenses comprising conducting materials, for example gold, platinum, aluminum, doped poly-silicon, silicon, titanium, nickel, chromium or any combination of these or other patternable conducting materials. Useful electrostatic lenses include lenses having a thickness selected from 0.01 to 5 µm.

For specific embodiments, a chemical sensor device comprises a first passivation layer positioned between the electrostatic lens electrode and the source and the drain of the semiconductor field effect sensor for electrically isolating the electrostatic lens electrode from the source and the drain. The first passivation layer may, for example, be at least partially disposed on the sensing region for immobilizing one or more probe molecules above the sensing region. In embodiments, a passivation layer has a thickness selected from 0.01 to 5 µm. The first passivation layer may also have a reduced thickness above the sensing region, for example a thickness selected from 0.001 to 0.1 µm.

For some embodiments, an electrostatic lens electrode includes a first opening above the sensing region for passing the one or more analytes to be sensed to the sensing region. In related embodiments, the first passivation layer optionally includes an opening or a reduced thickness above the sensing region for passing the one or more analytes to be sensed to the sensing region. In a specific embodiment, a chemical sensor device further comprises a second passivation layer located on the electrostatic lens electrode, wherein the second passivation layer includes an opening above the sensing region for passing the one or more analytes to be sensed to the sensing region. The openings above the sensing region may independently have, for example, a cross-sectional dimension selected from 0.1 to 50 µm.

Useful passivation layers include layers comprising insulating materials or other materials. In embodiments, a passivation layer comprises oxygen and/or nitrogen, for example in the form of an oxide or a nitride layer such as $SiO_2$ or $Si_3N_4$. In a specific embodiment, at least a portion of a passivation layer has a composition having a stoichiometry of $MO_X$, wherein M is a semiconductor and x is selected from the range of 0-2. In a specific embodiment, at least a portion of a passivation layer has a composition having a stoichiometry of $MN_y$, wherein M is a semiconductor and y is selected from the range of 0-1.33. In embodiments, a passivation layer comprises silicon and/or a silicon rich layer, $SiO_2$, $Si_3N_4$, $SiO_xN_y$, $Al_2O_3$, $HfO_2$, AlN, polyimide, a photoresist, any insulator that can be deposited or grown on the semiconductor layer and/or any combination of these materials. In another embodiment, a passivation layer comprises a layer having a mixture of aluminum and oxygen. Useful insulating layers also include those comprising sapphire, glasses and/or plastics.

In a specific embodiment, a chemical sensor device comprises one or more probe molecules immobilized on the surface of the sensing region or the surface of the first passivation layer. A variety of probe molecules are useful with the chemical sensor devices described herein for chemical/biochemical sensing. For example, useful probe molecules include molecules selected from the group consisting of DNA, LNA, PNA, RNA, aptamers, other nucleic acid analogs, proteins, amino acids, and any combination of these or other ligands. For a specific embodiment, a chemical sensor device is provided as a pH sensor. For embodiments where the probe molecules are immobilized on the surface of the first passivation layer, the composition of the first passivation layer may be selectively adjusted for immobilization of a particular probe molecule. For example, the first passivation layer may comprise $SiO_2$, $Si_3N_4$, $Si_xN_y$, $Al_2O_3$, $HfO_2$, and/or AlN in varying amounts for selective immobilization of a probe molecule.

The chemical sensor devices provided herein are useful as individual elements in an array of chemical sensors; for example an N×N array of chemical sensor devices. In a specific embodiment, each chemical sensor device element of the array is independently electrically addressable. For example, the source, drain, gate, and/or electrostatic lens electrode of each chemical sensor device element in an array of chemical sensors may be individually electrically addressable. In another embodiment, the sensing regions of each chemical sensor device element may be independently fluidly addressable; that is, a fluid may be provided to the sensing region of a single chemical sensor device element independently from other chemical sensor device elements.

According to another aspect, a method is provided for single molecule detection for RNA, DNA, LNA, PNA, aptamers, proteins, or other molecules. A method of this aspect comprises the steps of: providing a field effect sensor comprising an electrostatic lens electrode, a gate electrode and a sensing region, wherein the sensing region is functionalized to detect a target analyte molecule; providing a solution to the field effect sensor, wherein the solution comprises a plurality of analyte molecules including at least one target analyte molecule; applying a first potential difference between the electrostatic lens electrode and the gate electrode to attract a target analyte molecule to the sensing region; monitoring an electric parameter of the field effect sensor to determine when a single target analyte molecule is detected by the field effect sensor; and applying a second potential difference between the electrostatic lens electrode and the gate electrode to repel additional analyte molecules from the sensing region. In a specific embodiment, the second potential difference is of the opposite sign of the first potential difference. In a specific embodiment, the electrostatic lens electrode includes an opening above the sensing region for passing the one or more analytes to be sensed to the sensing region.

In another aspect, a method and device are provided for amplifying a single target molecule, for example by PCR. A method of this aspect comprises the steps of: providing a field effect sensor comprising an electrostatic lens electrode, a gate electrode, a source, a drain and a sensing region, and wherein the sensing region is functionalized for detection of a target analyte molecule by the field effect sensor; providing a solution to the field effect sensor, wherein the solution comprises a plurality of analyte molecules including at least one target analyte molecule; applying a first DC voltage between the electrostatic lens electrode and the gate electrode to attract a target analyte molecule to the sensing region; monitoring an electric parameter of the field effect sensor to determine when a single target analyte molecule is detected by the field effect sensor; applying a second DC voltage between the electrostatic lens electrode and the gate electrode to repel additional analyte molecules from the sensing region, wherein the second DC voltage is of the opposite sign of the first DC voltage; and repeating one or more times the steps of: applying a first AC voltage between the gate electrode and the source and drain to raise the temperature of the target analyte molecule to a first temperature; terminating the application of voltage between the gate electrode and the source and drain and allowing the temperature of the target analyte molecule to relax to a second temperature; and applying a second AC voltage between the gate electrode and the source and drain to raise the temperature of the target analyte molecule to a third temperature. In a specific embodiment, an electric parameter of the field effect sensor is monitored to determine a quantity increase of the target analyte molecule achieved during the repeating steps. In an embodiment, an electric parameter of the field effect sensor is monitored to determine a change in pH achieved during the repeating steps. Certain embodiments further comprise applying a DC and/or AC voltage between the electrostatic lens electrode and the gate electrode, for example to concentrate the molecules and/or keep them at/close to the gate/sensing region during and/or after amplification; for some embodiments, this step is optionally repeated. In a specific embodiment, a negative voltage is applied to the electrostatic lens electrode to keep the amplified molecules at and/or close to the gate electrode and/or sensing region.

For some methods of this aspect, the solution further comprises components and reagents necessary for performing PCR on the single target analyte molecule. Additionally, methods of this aspect may further comprise the step of providing a second solution to the field effect sensor before the repeating steps, wherein the second solution comprises components and reagents necessary for performing PCR on the single target analyte molecule.

Steps of the methods described herein may occur simultaneously or in any order. For example, the monitoring step may occur prior to, during, and after the application of the first potential difference. In an embodiment, the step of applying the second potential difference occurs immediately after the detection of the target analyte during the monitoring step. In a related embodiment, if a target analyte molecule is detected before the application of the first potential difference, the second potential difference is immediately applied.

Useful electric parameters include, but are not limited to, a resistance and/or a conductance across the field effect sensor, a current through the field effect sensor, a potential of the field effect sensor, an AC impedance of the field effect sensor, or any combination of these or other electrical properties. Monitoring of these and other electric parameters is useful, for example, for sensing a change in pH, an increase or decrease in charge at the sensing region and/or the presence or absence of an analyte molecule or a portion of an analyte molecule at the sensing region. A specifically useful electric parameter is the impedance of the solution. The impedance of the solution can be measured, for example, through the electrostatic lens electrodes or the gate electrodes. U.S. Provisional Patent application 61/245,083 filed on Sep. 23, 2009, which is hereby incorporated by reference in its entirety, discloses methods of detection of amplification of molecules by measuring the impedance of a solution.

In an embodiment, a method of this aspect for amplification of a target molecule by PCR comprises the steps of providing a chemical sensor device, for example as described above; providing a solution containing at least one target molecule to a surface of the chemical sensor device, providing a preselected AC voltage between a gate and a source and a drain of the chemical sensor device to heat the chemical sensor device to a preselected temperature; and transporting the at least one target molecule across the surface of the chemical sensor device.

In a specific embodiment, the transporting step includes moving the at least one target molecule through a spatial temperature gradient. Useful thermal gradients include those which include the temperatures necessary for performing PCR on the at least one target molecule. For example, the spatial temperature gradient can include a denaturation temperature (such as from 90 to 100° C.), an extension temperature (such as from 68 to 75° C.) and an annealing temperature (such as from 45 to 60° C.).

Transport of the target molecules across the spatial temperature gradient provides for sequentially the placing target molecules into the necessary temperatures for amplification. Useful transport processes include active and passive transport, for example transport by diffusion, transport by dielectrophoresis, electro-osmotic flows or any combination of these or other electro-thermal transport processes.

In another aspect, the methods and devices described herein may be utilized in the sequencing of a nucleic acid molecule or group of nucleic acid molecules. A method of this aspect comprises the steps of: providing the nucleic acid to be sequenced; fragmenting the nucleic acid to be sequenced into a plurality of fragments; providing an array of chemical sensors; loading the plurality of fragments into the chemical sensor device elements of the chemical sensor array; and monitoring an electric parameter of each of the chemical sensor device elements to determine the sequence of the plurality of fragments. For example, the monitoring step may include sensing a change in the charge present at the sensing region of each chemical sensor device element as complements to the plurality of fragments are synthesized. A method of this aspect further comprises the step of providing to the chemical sensor device elements the necessary reagents for the synthesis of the complements to the fragments, for example nucleic acids and/or replication enzymes such as a polymerase. In a specific embodiment, an electric parameter of the field effect sensor is monitored to determine a change in pH achieved during synthesis.

For some applications, in the loading step, each sensor device element is loaded with no more than one fragment. In a specific method of this aspect, in the loading step, a first DC voltage is applied between the electrostatic lens electrode and the gate electrode of each chemical sensor device element to attract fragments to the sensing regions of the chemical sensor device elements. This method may further comprise the steps of monitoring an electrical parameter of the chemical sensor device elements to detect when a single fragment is loaded into an individual chemical sensor device element; and applying a second DC voltage between the electrostatic lens electrode and the gate electrode of the individual chemical sensor device element to repel additional fragments, wherein the second DC voltage is of the opposite sign of the first DC voltage.

Depending upon the sensitivity of the chemical sensor device elements, the plurality of fragments loaded into the chemical sensor device elements may be amplified, for example by PCR. In a specific embodiment of this aspect, an amplification step includes repeating one or more times the steps of: applying a first AC voltage between the gate electrode and the source and drain of the individual chemical sensor device elements to raise the temperature of the fragments to a first temperature; terminating the application of voltage between the gate electrode and the source and drain of the individual chemical sensor device elements and allowing the temperature of the fragments to relax to a second temperature; and applying a second AC voltage between the gate electrode and the source and drain of the individual chemical sensor device elements to raise the temperature of the fragments to a third temperature. When performing PCR on the fragments, in an embodiment, the necessary components and reagents are provided to the chemical sensor device elements. If desired, an electric parameter of the field effect sensors of the individual chemical sensor device elements may be monitored to determine a quantity increase of the fragments achieved during amplification. In an embodiment, an electric parameter of the field effect sensor is monitored to determine a change in pH achieved during amplification.

Some methods of this aspect further comprise the step of heating the chemical sensor device elements of the chemical sensor array to bind the fragments to the sensing regions of the chemical sensor device elements. For example the heating may be achieved by applying a first AC voltage between the gate electrode and the source and drain of individual chemical sensor device elements.

In another aspect, a method is provided for sensing a structure containing nucleic acids, for example a cell (e.g., a plant cell, mammalian cell, or bacterial cell), a spore, and/or a virus. A method of this aspect comprises the steps of: providing a chemical sensor device, for example as described herein; and providing a solution having one or more nucleic acid containing structures to the chemical sensor device. If desired, an electrical parameter of the chemical sensor device is monitored to detect when a nucleic acid containing structure is loaded into the chemical sensor device. In some embodiments one nucleic acid containing structure is loaded into a chemical sensor device; in other embodiments a plurality of nucleic acid containing structures are loaded into a chemical sensor device.

A method of this aspect for trapping a nucleic acid containing structure further comprises the step of providing a first DC voltage between an electrostatic lens electrode and a gate electrode of the chemical sensor device element to attract and/or trap the nucleic acid containing structure. A method of this aspect further comprises the step of providing a second DC voltage between the electrostatic lens electrode and the gate electrode of the chemical sensor device element to repel additional nucleic acid containing structures.

A specific method of this aspect further comprises the step of heating and/or lysing the nucleic acid containing structure to release the nucleic acid, for example by providing an AC voltage between the gate electrode and a source and drain of the chemical sensor device. For example, the nucleic acid containing structure is heated to 95-100° C. for 4-6 minutes to lyse the structure. Once the nucleic acids are released, in an embodiment, they are amplified and/or detected using the methods and/or devices described herein. In a specific embodiment, the nucleic acids are amplified and/or detected using the same chemical sensor device or element used to heat and/or lyse the nucleic acid containing structure.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

DETAILED DESCRIPTION OF THE INVENTION

Figure 1:
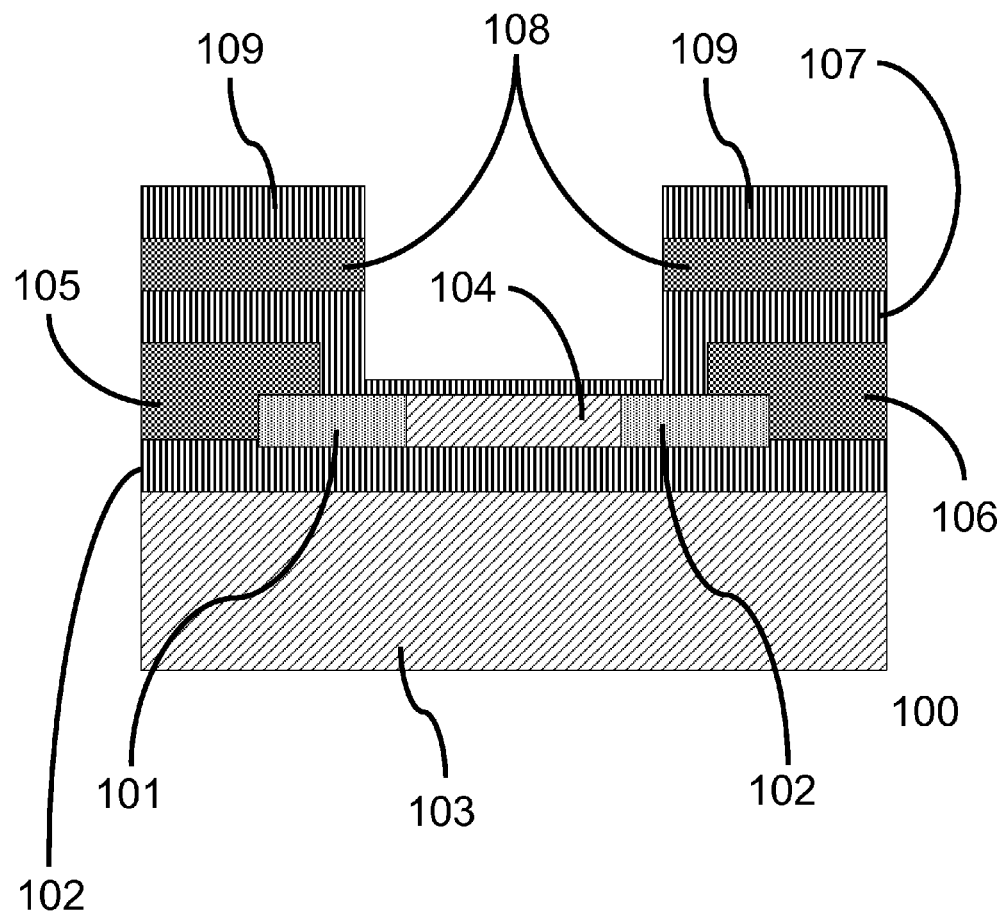
FIG. 1 illustrates an exemplary chemical sensor device.

In general the terms and phrases used herein have their art-recognized meaning, which can be found by reference to standard texts, journal references and contexts known to those skilled in the art. The following definitions are provided to clarify their specific use in the context of the invention.

"Field effect sensor" refers to a semiconductor device, similar to a field effect transistor, in which the conductivity of a channel in the semiconductor is modified by the presence of analyte molecules near the surface of a sensing region.

"Nanoplate" refers to a sensing region of a field effect sensor having a specific shape, for example a planar or substantially planar and rectangular shape.

"Nanowire" refers to a sensing region of a field effect sensor having a specific shape, for example a cylindrical or substantially cylindrical shape, similar to that of a wire.

"PCR" or "Polymerase chain reaction" refers to the well known technique of enzymatic replication of nucleic acids which uses thermal cycling for example to denature, extend and anneal the nucleic acids.

"Loading" or "loaded" refers to providing a molecule, compound, substance or structure to the sensing region or a well adjacent to or above the sensing region of a chemical sensor device.

The chemical sensor devices disclosed herein are useful, for example, for detection and/or sequencing of nucleic acids. According to one aspect, the devices include an electrostatic lens for attracting and trapping, for example by a DC electric field, a single target nucleic acid chain for selective amplification and detection and/or sequencing. According to another aspect, the devices utilize an AC voltage for dielectric heating of the nucleic acid molecules. The temperature profile above the devices can be utilized in a passive manner, for example, for amplification of nucleic acid molecules by transporting the nucleic acid molecules through the temperatures necessary for amplification by PCR. The temperature above the devices can also, for example, be used in a more active manner by providing a sequence of AC voltages to heat the nucleic acid molecules to the temperatures necessary for amplification by PCR.

The methods and devices described herein are additionally or alternatively useful for nucleic acid amplification in addition to PCR, for example by using techniques known in the art. For example, Nucleic Acid Sequence Based Amplification (NASBA) and/or Loop mediated isothermal amplification (LAMP) may be used to amplify a target nucleic acid molecule. NASBA is a useful technique, as it is an isothermal amplification technique and does not require the numerous heating and cooling steps that PCR requires. Methods described herein for amplifying a target nucleic acid molecule using a method with one or more heating and/or cooling steps (e.g., a PCR method) can be modified to alternatively use isothermal amplification techniques (e.g,. NASBA) by providing the necessary enzymes, synthetic reagents and/or physical conditions (temperature, concentration, pH, etc.).

FIG. 1 shows an embodiment of a chemical sensor device 100. Chemical sensor device 100 includes a field effect sensor having a source region 101, a drain region 102, a gate region 103 and a sensing region 104. Electrodes 105 and 106 respectively allow for electrical connections to be made to source region 101 and drain region 102. A first passivation layer 107 is disposed on the field effect sensor, providing electrical isolation between the field effect sensor and an electrostatic lens electrode 108. Electrostatic lens electrode 108 includes an opening above sensing region 104 to allow target analytes to pass through to sensing region 104. First passivation layer 107 has a reduced thickness portion adjacent to sensing region 104. Such a reduced thickness can, for example, allow target analytes to more strongly interact with and be detected by sensing region 104. A second passivation layer 109 is disposed over electrostatic lens electrode 108.

Figure 2A:
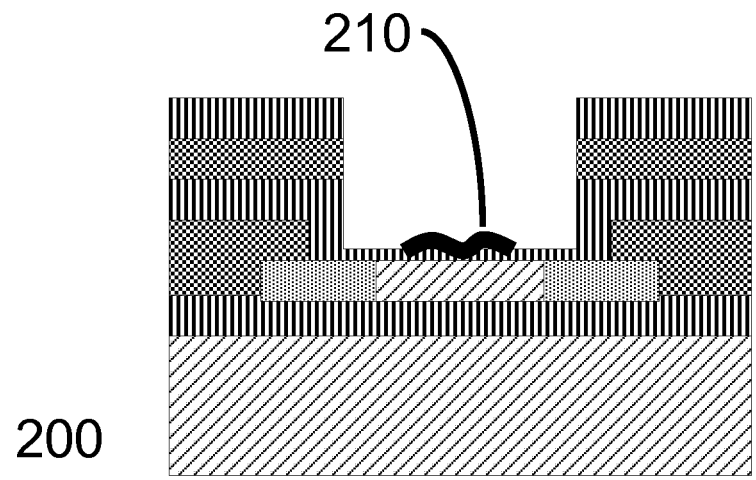
FIGS. 2A-2D illustrate an embodiment of a method for detection of a single target analyte molecule.
Figure 2B:
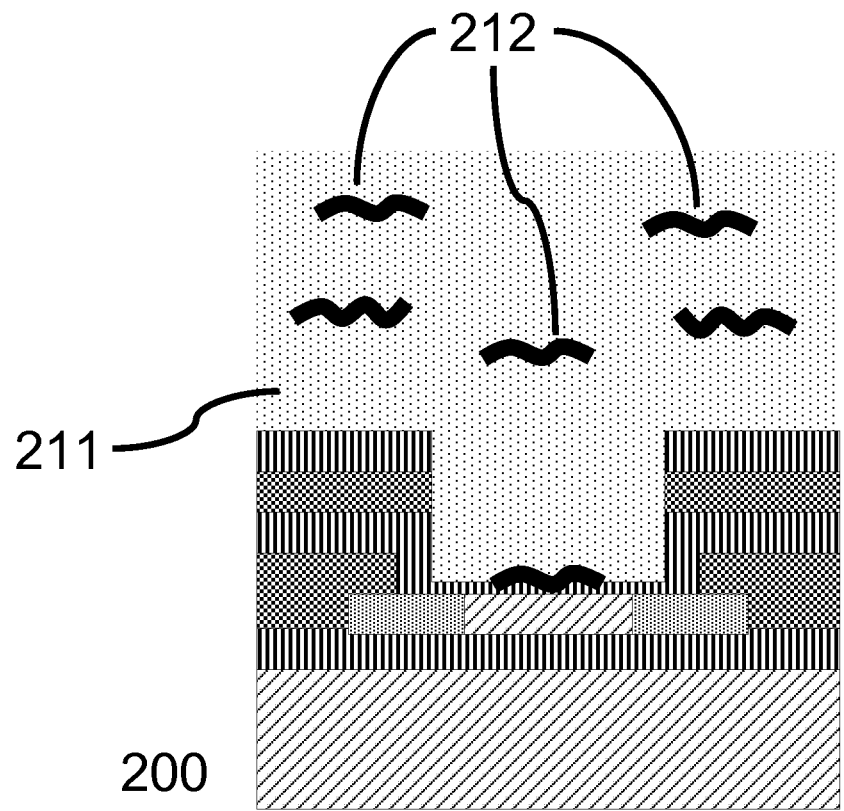
Figure 2C:
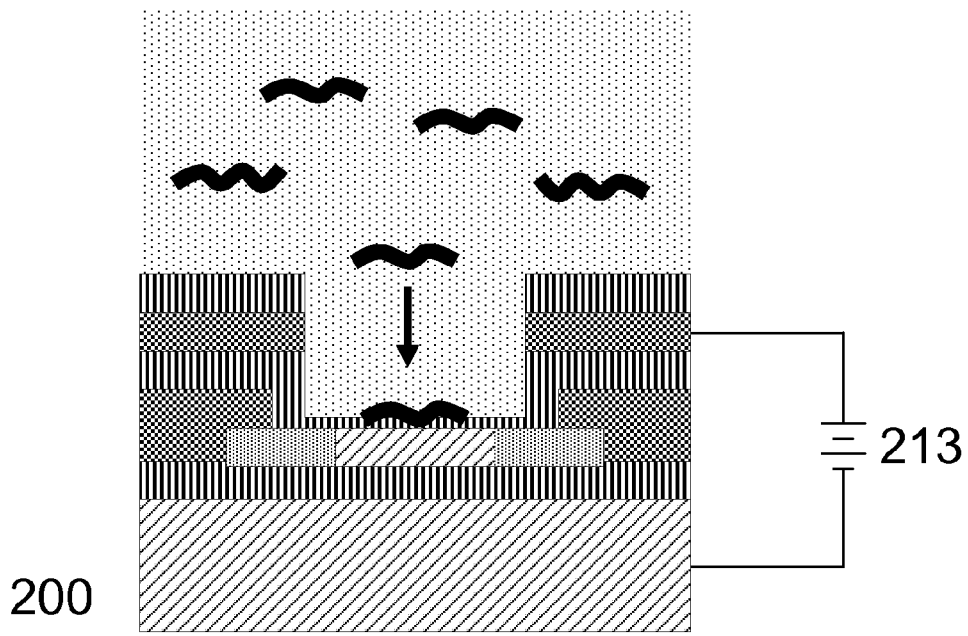
Figure 2D:
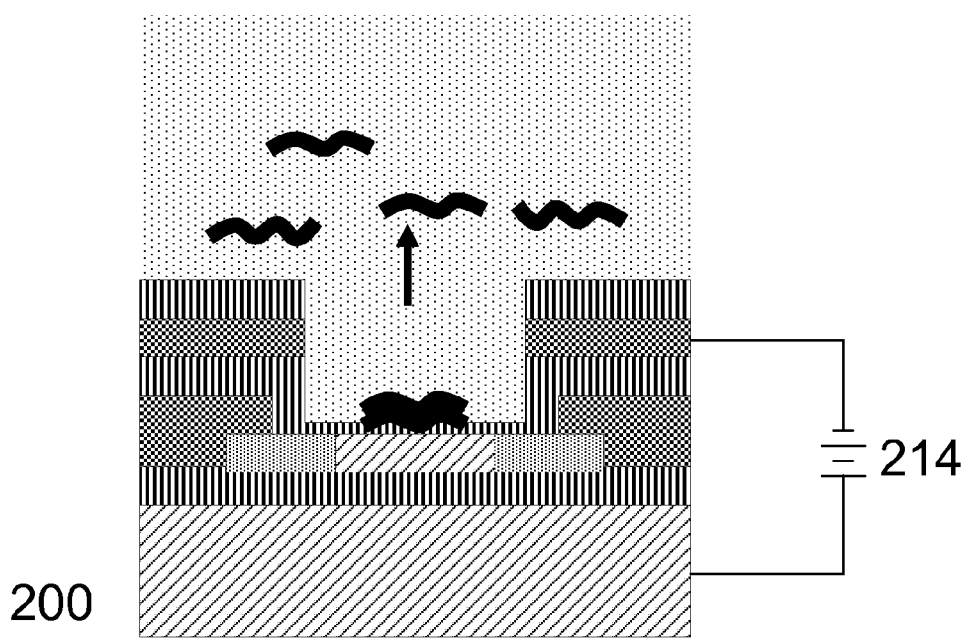

FIGS. 2A-2D illustrate an embodiment of a method for detection of a single target analyte molecule. FIG. 2A shows a chemical sensor device 200 having the sensing region functionalized with a probe molecule 210 for detection of the target analyte molecule. As shown in FIG. 2B, a solution 211 having analyte molecules is provided to the chemical sensor device. In this example, three target analyte molecules 212 are included in solution 211. In FIG. 2C, a first potential difference 213 is applied between the electrostatic lens electrode and the gate to attract analyte molecules toward the sensing region, as indicated by the arrow. An electric parameter of the field effect sensor is monitored, for example the conductance between the source and the drain, and when it is determined that a single target analyte molecule is detected, a second potential difference 214, having the opposite sign as the first potential difference, is applied between the electrostatic lens electrode and the gate to repel additional molecules from the sensing region, as shown in FIG. 2D.

Figure 3A:
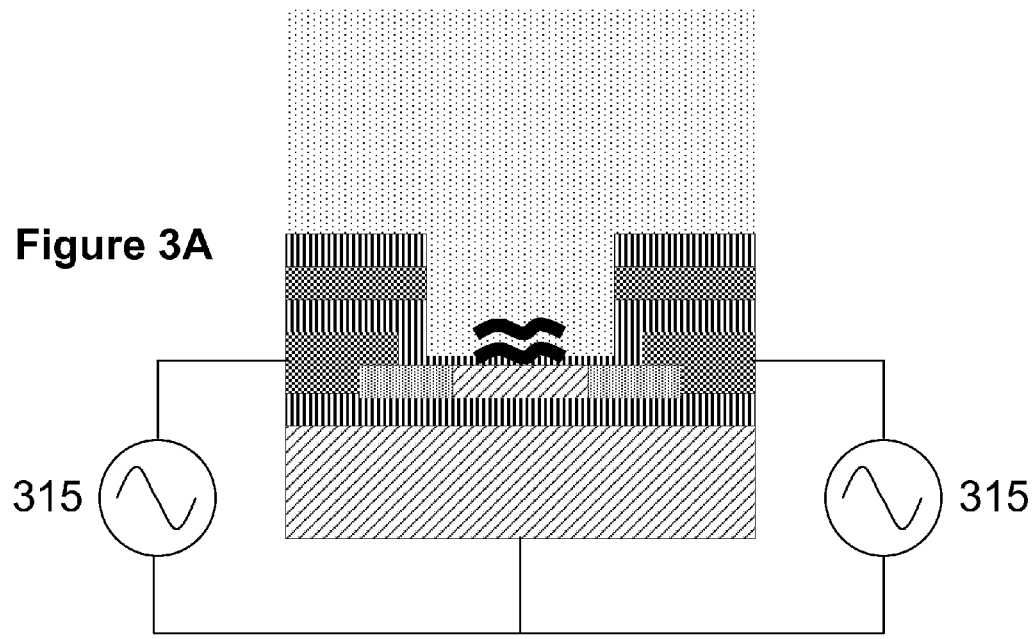
FIGS. 3A-3C illustrate additional steps for amplification of a target analyte molecule by PCR.
Figure 3B:
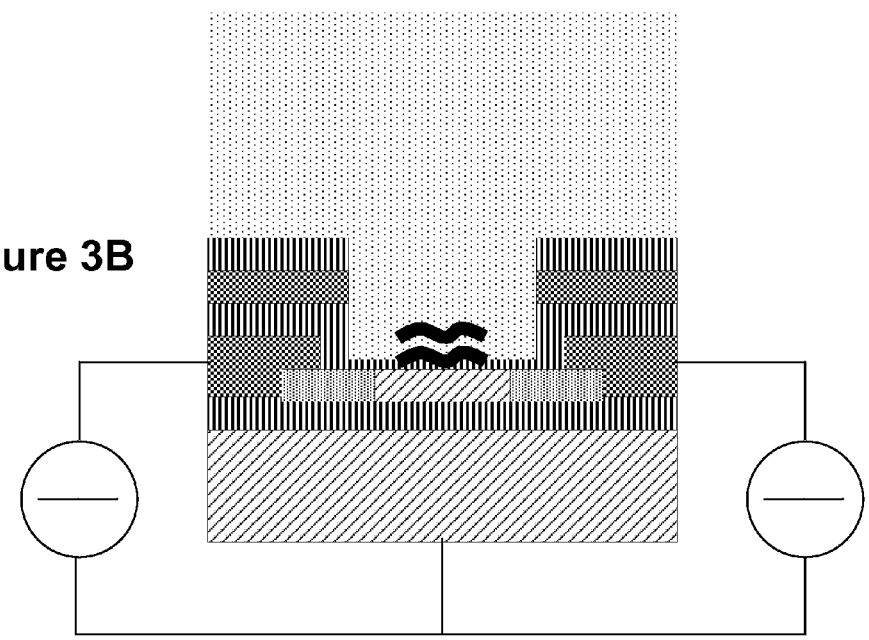
Figure 3C:
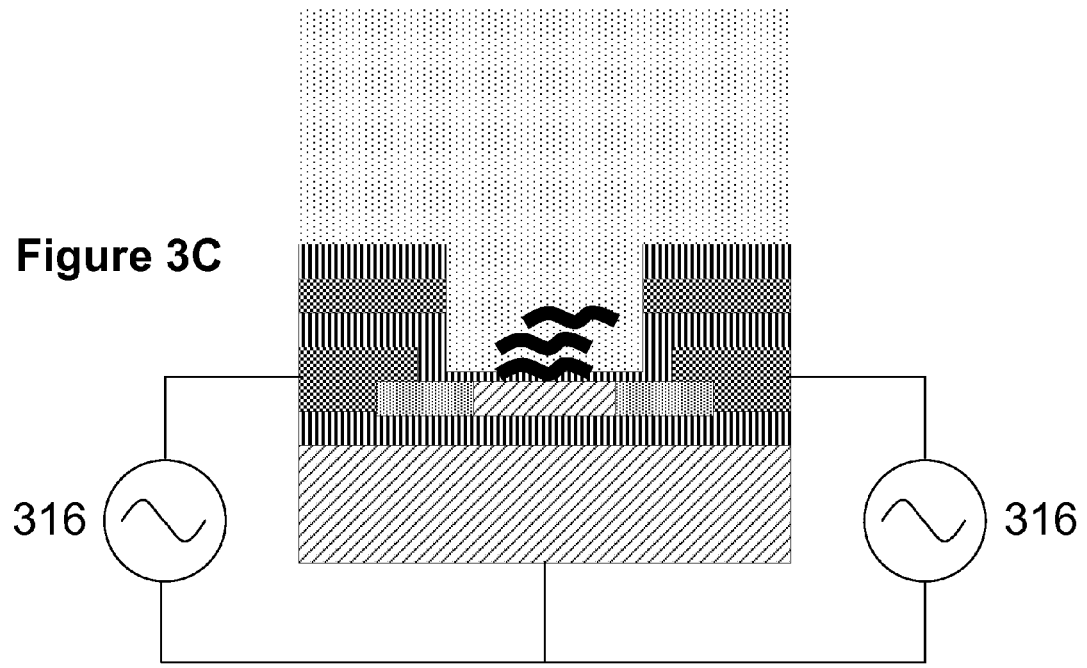
Figure 3D:
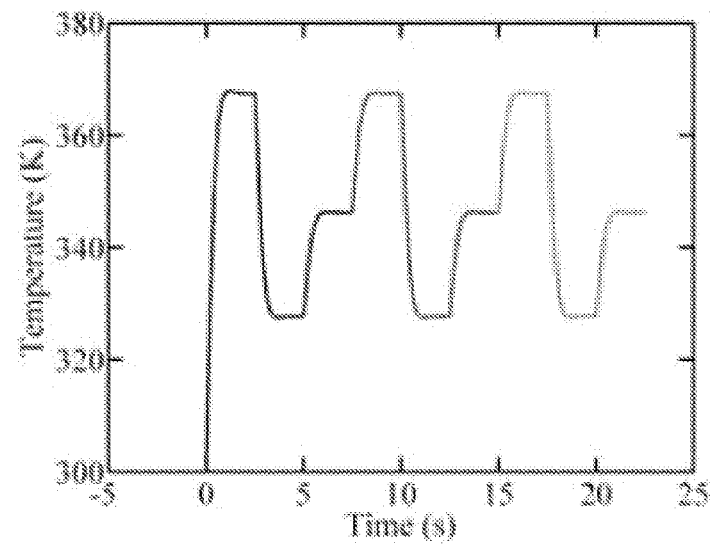
FIG. 3D shows an example temperature profile achieved by this method.

The method of FIGS. 2A-2D may be further utilized with additional steps for amplification of a target analyte molecule by PCR, as illustrated by FIGS. 3A-3C. Once a single target analyte molecule is detected, as in FIG. 2D, the first subsequent step is application of a first AC voltage 315 between the gate and the source and drain to increase the temperature of the target analyte molecule, as shown in FIG. 3A. After the target analyte molecule reaches a first desired temperature, the voltage is terminated, as shown in FIG. 3B, to allow the temperature of the target analyte molecule to relax. After the target analyte molecule reaches a second desired temperature, a second AC voltage 316 is applied between the gate and the source and drain to increase the temperature of the target analyte molecule, FIG. 3C. After the target analyte molecule reaches a third desired temperature, the steps shown in FIGS. 3A-3C may be optionally repeated to further amplify the target analyte molecule. FIG. 3D shows an example temperature profile which is achieved by this method.

Figure 4A:
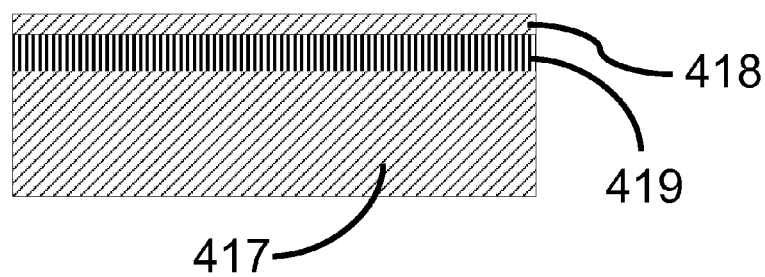
FIGS. 4A-4R illustrate a cross-sectional process flow of an embodiment of a method for fabrication of a chemical sensor device.
Figure 4B:
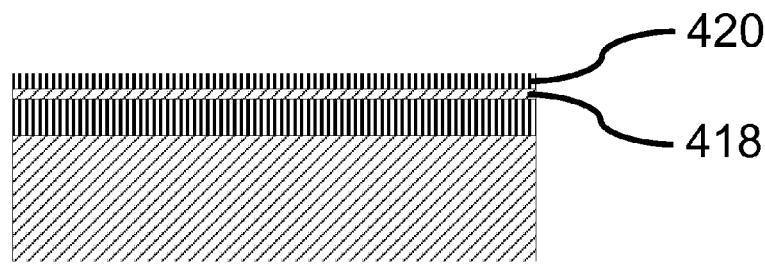
Figure 4C:
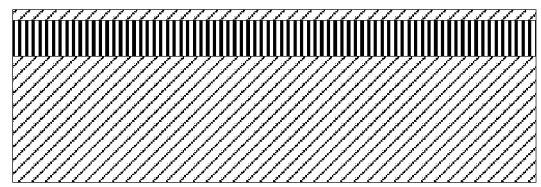
Figure 4D:
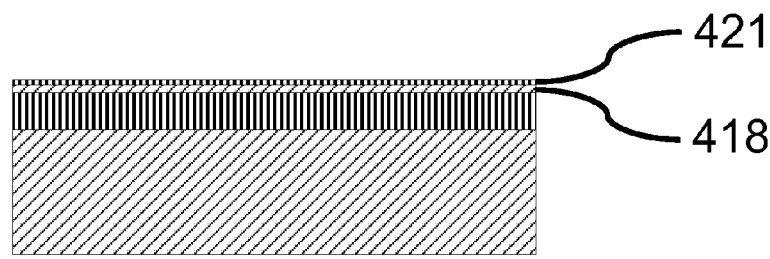
Figure 4E:
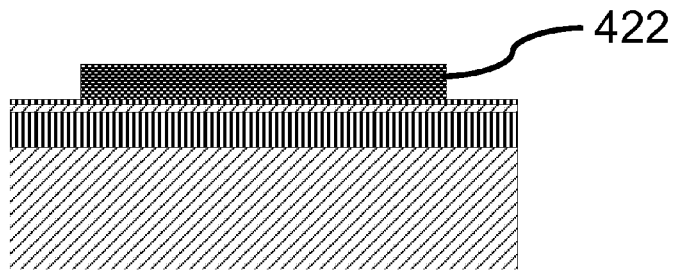
Figure 4F:
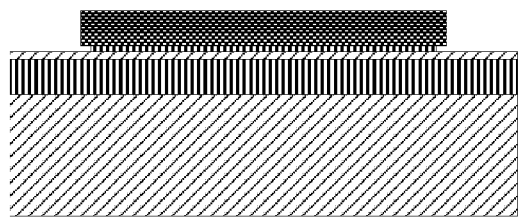
Figure 4G:
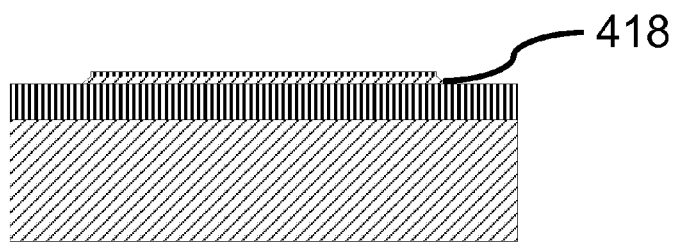
Figure 4H:
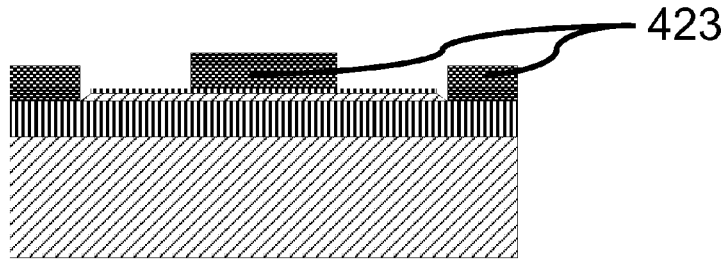
Figure 4I:
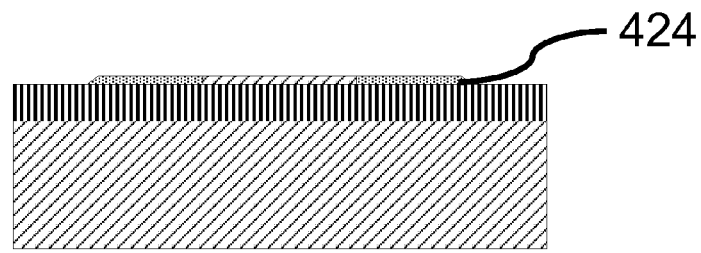
Figure 4J:
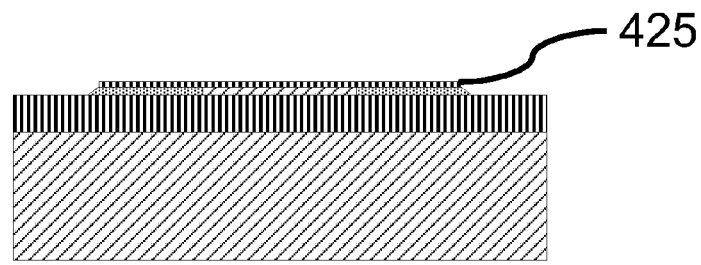
Figure 4K:
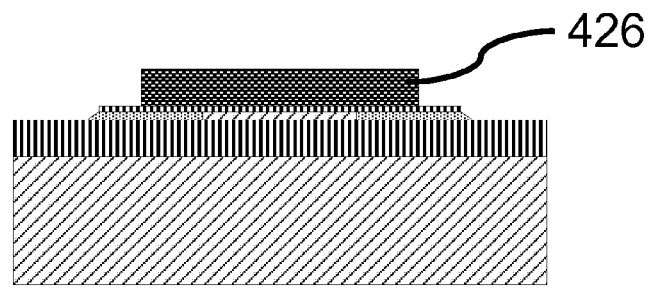
Figure 4L:
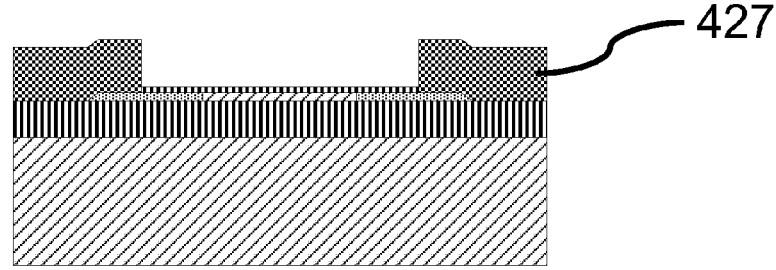
Figure 4M:
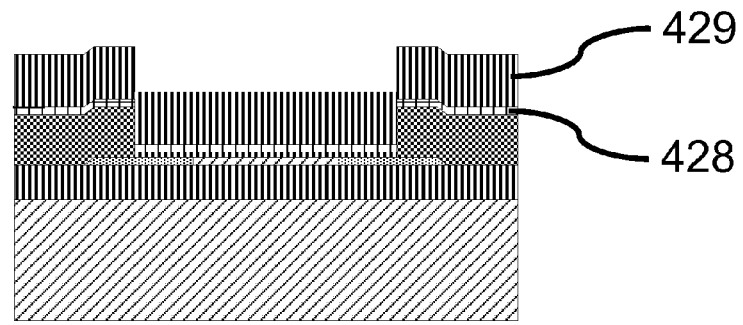
Figure 4N:
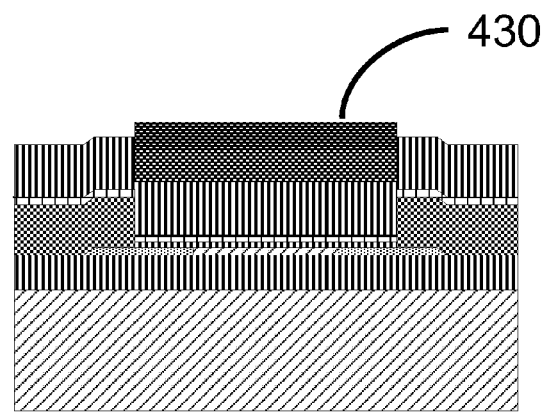
Figure 4O:
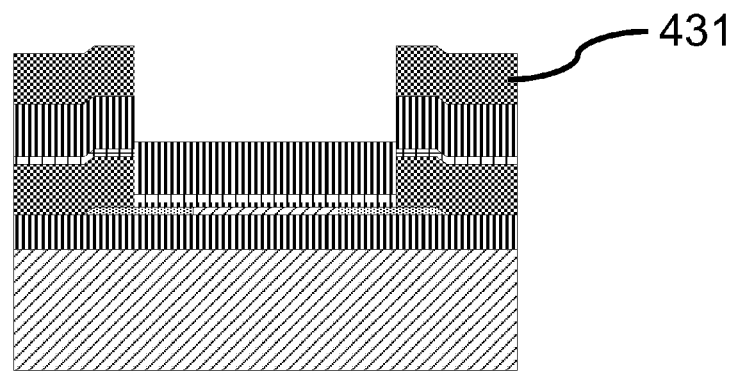
Figure 4P:
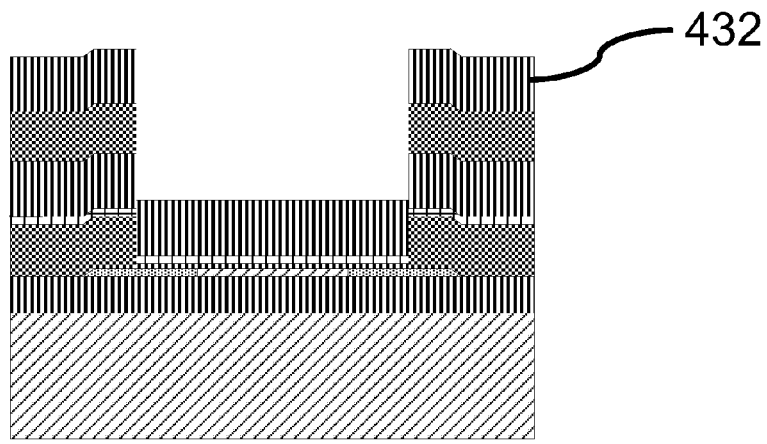
Figure 4Q:
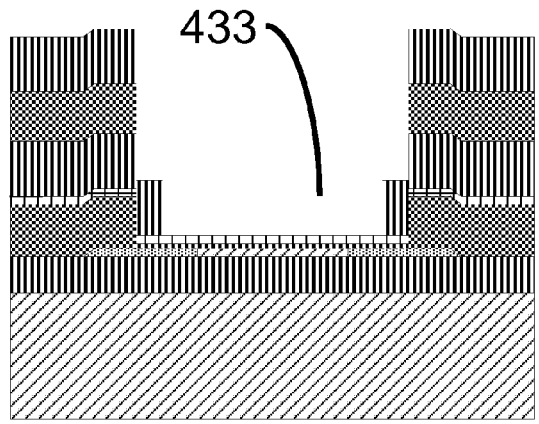
Figure 4R:
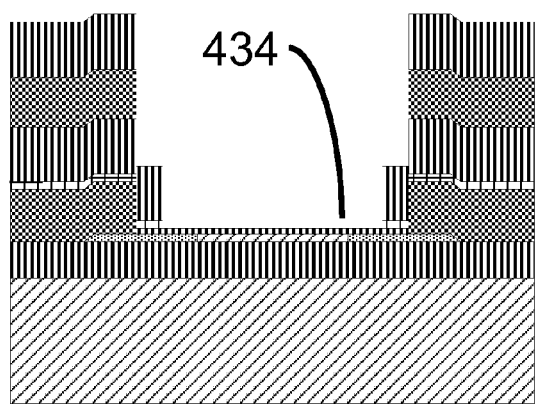

FIGS. 4A-4R illustrate a cross-sectional process flow of an embodiment of a method for fabrication of a chemical sensor device. Necessary processing materials, techniques and devices will be evident to those having skill in the art.

FIG. 4A: This process begins with a silicon-on-insulator (bonded) wafer with substrate 417 and having a top silicon layer 418 and a buried oxide layer 419. FIG. 4B: A dry oxide 420 is grown on the top silicon layer 418 to thin it down, leaving oxide 420. FIG. 4C: The oxide 420 is etched down to silicon layer 418. FIG. 4D: If desired, dry oxidation of the top silicon layer 418 thins it further, creating oxide 421. FIG. 4E: The active area is defined, for example using e-beam lithography, using a negative resist 422 and oxide 421 as a hard mask. FIG. 4F: The oxide 421 is etched, undercutting the resist slightly. FIG. 4G: The resist is removed and the active area silicon 418 is etched having a slight overcut. FIG. 4H: A photoresist mask 423 is deposited for subsequent implantation of dopants into silicon layer 418. FIG. 4I: Oxide 421 is etched after dopant implantation, exposing the silicon regions 424 having implanted dopants. FIG. 4J: A high quality gate oxide 425 is grown using dry oxidation. FIG. 4K: A mask 426 is placed over the active area. FIG. 4L: Metal contacts 427 are deposited over the implanted regions 424 and the mask 426 is removed. At this point a rapid thermal anneal may be used to anneal the contacts 427. FIG. 4M: A thin layer of silicon nitride 428 and nitride rich silicon oxide 429 are subsequently deposited. FIG. 4N: Another mask 430 is placed over the active area. FIG. 4O: A metal electrostatic lens electrode 431 is deposited over silicon oxide 429 and the mask removed. FIG. 4P: A silicon oxide passivation layer 432 is deposited. FIG. 4Q: The silicon oxide above the active area is removed from region 433, stopping on silicon nitride layer 428. FIG. 4R: The silicon nitride is etched from region 434, stopping on oxide 425.

Figure 5A:
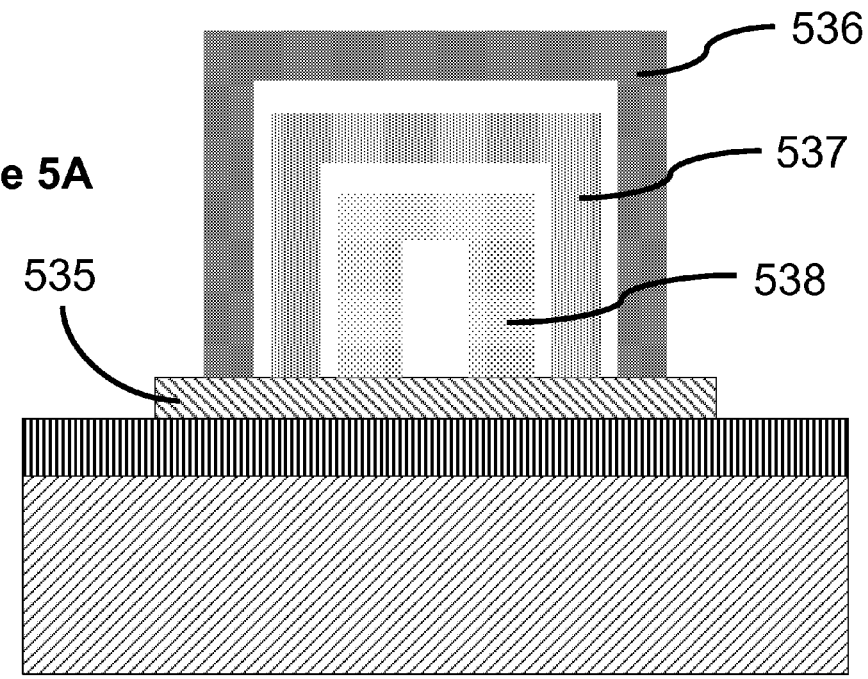
FIG. 5A illustrates three temperature regimes surrounding the active area of a chemical sensor device.
Figure 5B:
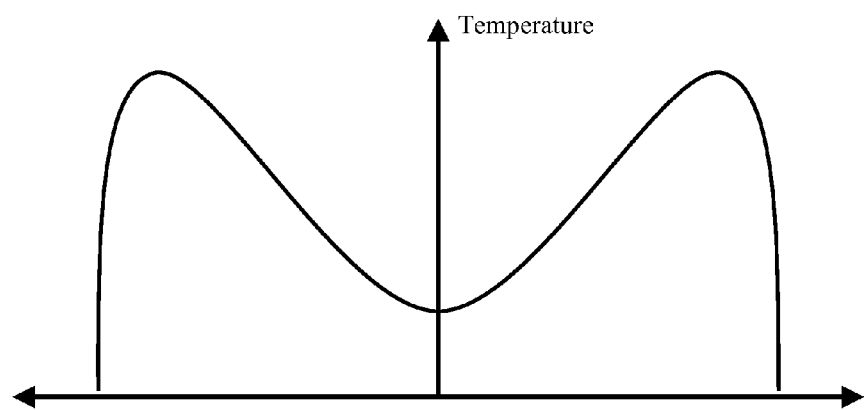
FIG. 5B shows a plot of the temperature as a function of the distance from the center of the active area.

FIG. 5A illustrates a device useful with embodiments of methods for amplification of a target analyte by PCR. When a preselected AC voltage is applied between the gate and the source and drain of the active area 535 of the device the temperature of the region surrounding the active area 535 is increased. Three general temperature regimes are created: a first temperature region 536, for example having a temperature under which nucleic acids can be denatured; a second temperature region 537, for example having a temperature under which denatured nucleic acids can be extended; and a third temperature region 538, for example having a temperature under which denatured and extended nucleic acids can be annealed. FIG. 5B shows a typical temperature profile of the device of FIG. 5A when a preselected AC voltage is applied between the gate and the source and drain regions.

In an embodiment, a solution containing target analytes to be amplified by PCR and other necessary PCR reagents is provided to the surface of a chemical sensor device, such as depicted in FIG. 5A. When a preselected AC voltage is applied between the gate and the source and drain regions of the chemical sensor device and the target analytes are transported across the chemical sensor device, the target analytes experience the three temperature regimes necessary for amplification by PCR. Transport of the analyte molecules can, for example, be by diffusion and/or dielectrophoresis.

Figure 6:
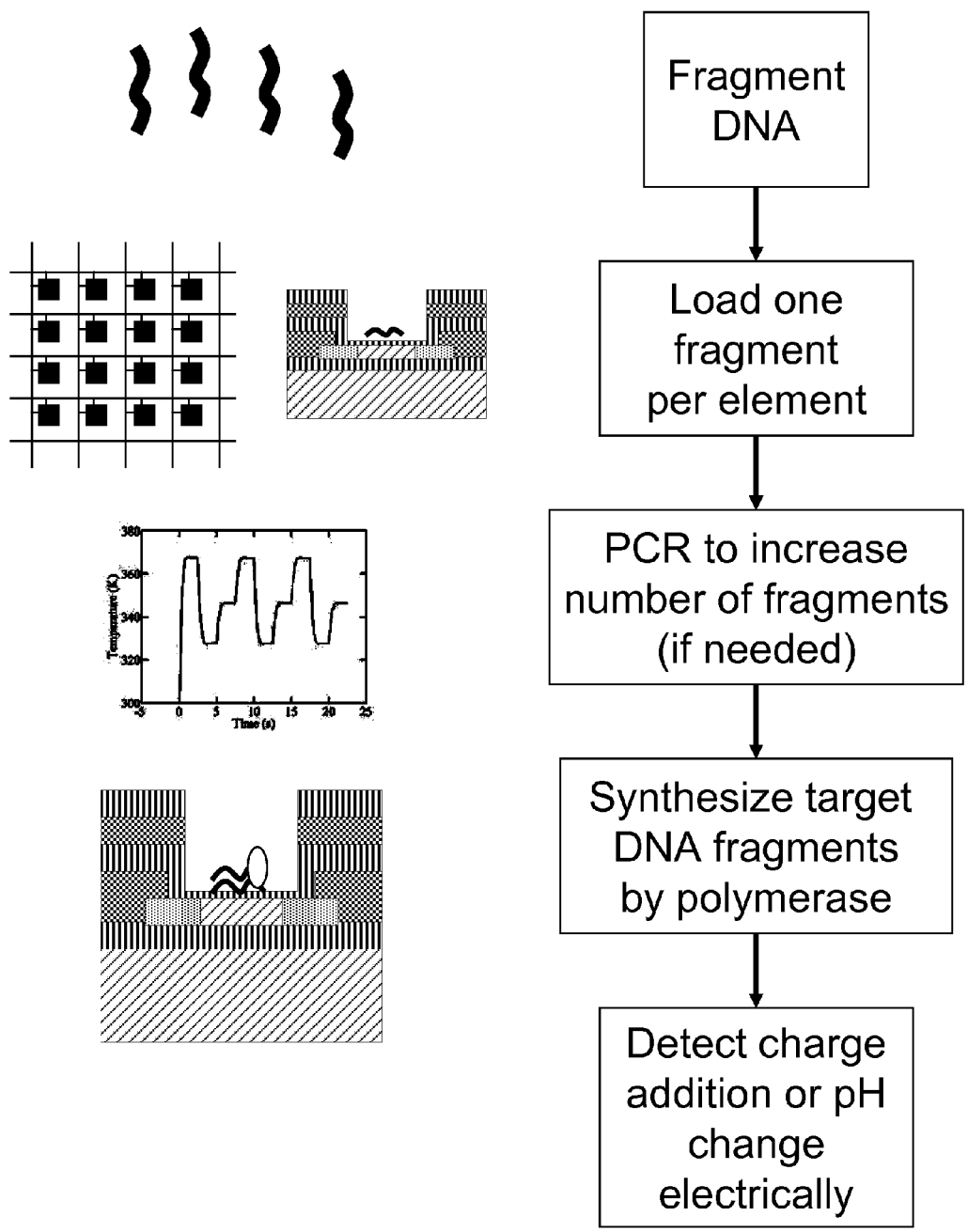
FIG. 6 illustrates a method for sequencing DNA, utilizing an N×N array of chemical sensor devices.

FIG. 6 illustrates the steps of a method for sequencing DNA using an NxN array of chemical sensor devices. Initially, the DNA is fragmented and single fragments are loaded into individual chemical sensor device elements. If needed, the fragments can be amplified using PCR by cycling of the temperature. Next, the complementary target fragments are synthesized using a DNA polymerase. While the target fragments are being synthesized, the charge provided by subsequent bases is monitored and detected, providing the sequence information for the fragments. Finally, the fragment sequence information is reassembled, providing the sequence of the initial DNA (not shown).

Figure 7:
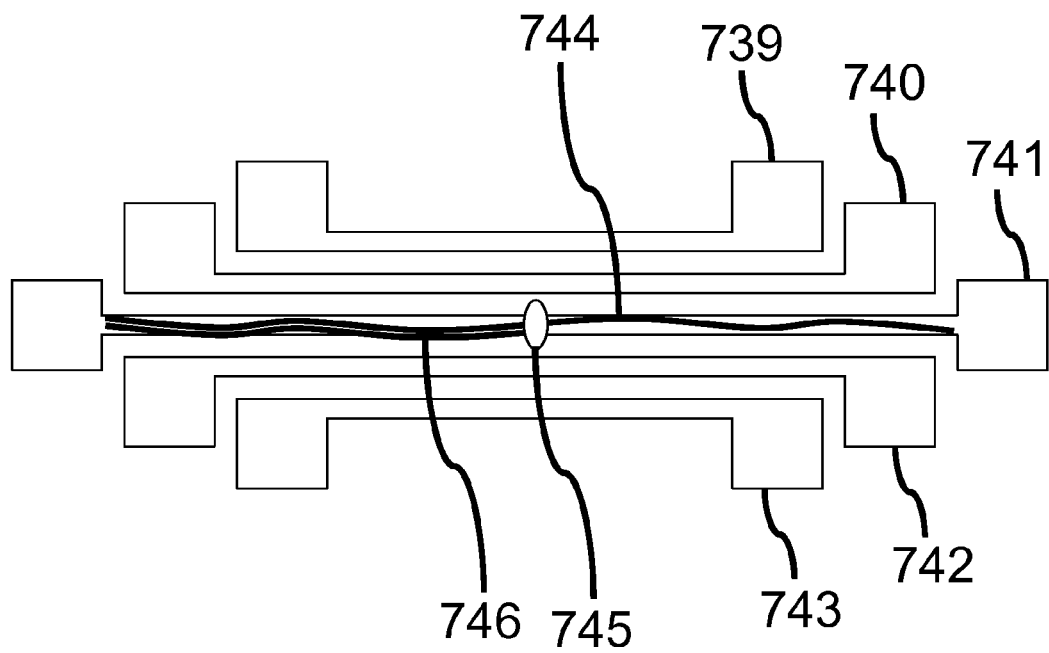
FIG. 7 illustrates a top down view of the arrangement of components in a chemical sensor device having multiple sensor portions.

In embodiments, multiple field effect sensors are used to isolate, detect, sequence and/or amplify a target molecule, for example a single target molecule. FIG. 7 illustrates a top down view of a specific sensor embodiment showing the arrangement of multiple field effect sensors in a side-by-side fashion, useful for detecting and/or amplifying a single DNA fragment. In this embodiment, five field effect sensors, 739, 740, 741, 742 and 743 are arranged side-by side. A target DNA fragment, 744, is attracted toward the sensing region where an enzyme 745, for example DNA polymerase, synthesizes a complementary DNA fragment 746. For certain embodiments, the complementary DNA fragment 746 is synthesized one base at a time by enzyme 745. In these and other embodiments, no amplification of the target DNA fragment 744 is necessary. For other embodiments, however, amplification of the target DNA fragment 744 by PCR or other techniques are contemplated.

In an exemplary embodiment, the field effect sensors 739, 740, 741, 742 and 743 are individually biased to attract and stretch DNA fragment 746 along field effect sensor 741. In one embodiment, field effect sensor 741 is biased at a first potential, $V_e$, while field effect sensors 739, 740, 742 and 743 are biased at a second potential of opposite sign, $-V_e$. In a specific embodiment, field effect sensor 741 is biased with different potentials at opposite sides of the sensor, e.g., $V_e+\Delta V$ at one end and $V_e-\Delta V$ at the opposite end. Without wishing to be bound by any theory, it is believed that when field effect sensors 739, 740, 741, 742 and 743 are biased in this manner, a lensing effect is created, attracting DNA fragment 746 toward and stretched along field effect sensor 741. In certain embodiments, field effect sensors 739, 740, 742 and 743 are biased at different potentials; for example, field effect sensors 740 and 742 can be biased at $-V_e$, while field effect sensors 739 and 743 can be biased at $-2V_e$. In other embodiments, field effect sensors 739, 740, 742 and 743 are not field effect sensors but are electrodes and/or electrostatic lenses.

The invention may be further understood by the following non-limiting examples:

EXAMPLE 1

Extremely Localized PCR with Temperature Cycling or PCR without Fluid Movement with Temperature Gradients Polymerase chain reaction (PCR) is a commonly used technique to amplify the amount of a nucleic acid sample analyzed by taking the sample through 3 temperature steps. These steps are for the annealing of the primer (lowest temperature), extension (the actual amplification, medium temperature) and denaturation of the product, which make up one cycle of the PCR. In each cycle the amount of nucleic acid is amplified twice the value before the cycle. By cycling many times, the nucleic acid at hand can be amplified orders of magnitude.

Dielectric heating capability of the devices described herein can be used for performing PCR, in an extremely localized fashion. A device can simply be cycled through the temperatures needed for the PCR to take place for amplification by changing the magnitude of the applied bias. Extremely localized heating allows for fast cycling due to the extremely low thermal mass associated, enabling nucleic acid amplification of many orders of magnitude in timescales less than a minute.

Alternatively PCR on the device can be performed by taking advantage of the thermal gradient that the heating method inherently provides. In this scheme the three temperatures needed for PCR are present on the device at spatially distinct locations, as shown in FIG. 5A. Thus, by passively or actively transporting the molecules to different locations of the device a PCR cycle can be completed. The passive transport of the molecules can be accomplished simply by the diffusion of the molecules. The molecules can be trapped in the device area by the potential barrier already setup due to the alternating electric field caused by dielectrophoresis (DEP). The active transport of molecules can be accomplished by designing the device geometry and in order to balance the thermal and electrical forces.

REFERENCES

U.S. Patent Application Publication No. 2006/0197118
U.S. Pat. Nos. 7,385,267 and 7,129,554
U.S. Patent Application Publication No. 2007/0292855
U.S. Pat. No. 6,203,683
U.S. Pat. No. 5,430,347
Notomi T, et al. 2000. Loop-mediated isothermal amplification of DNA. Nucleic Acids Research 28:E63
Compton J., Nucleic acid sequence-based amplification. Nature. 1991; 350(6313):91-2.
Baker-Jarvis, J., Jones, C. A., Riddle, B., NIST Technical Note 1509, 1998.
Bashir, R., Advanced Drug Delivery Review, Special issue: Intelligent Therapeutics: Biomimetic Systems and Nanotechnology in Drug Delivery, Edited by N. A. Peppas, Vol 56/11 pp 1565-1586, 2004.
Belgrader, P., Benett, W., Hadley, D., Richards, J., Stratton, P., Mariella, R., Milanovich, F., Science, 1999, 284, 449-450.
Berdat, D., Marin, A., Herrera, F., Gijs, M. A. M., Sensors and Actuators B, 118, 53 (2006).
Bhattacharya, S., Salamat, S., Morisette, D., Banada, P., Akin, D., Liu, Y., Bhunia, A. K., Ladisch, M., and Bashir, R., Lab Chip, 2008, 8, 1130-1136.
Chen, Z.-H., Butler, W. R., Bumstark, B. R., and Ahearn, D. G., Journal of Clinical Microbiology, 1996, 34, 1267-1269.
Cheng, X., Liu, Y., Dimirci, U., Irimia, D., Yang, L., Zamir, L., Rodriguez, W., Toner, M., Bashir, R., Special Issue on Cells and Tissue in Microsystems, Lab. Chip., 2007, 7, 746-755.
Chrisey, L. A., Lee, G. U., & O'Ferrall, C. E., "Covalent attachment of synthetic DNA to self-assembled monolayer films". Nucleic Acids Research Vol. 24, pp. 3031-3039, 1996.
Cui, Z., Zhao, Z., and Xia, S., Proceedings of SPIE, 2001, 4407, 275-280.
El-Ali, J., Perch-Nielsen, I. R., Poulsen, C. R., Bang, D. D., Telleman, P., Wolff, A., Sensors and Actuators A, 2004, 110, 3-10.
Elibol, O. H., Reddy, B., Nair, P. R., Bergstrom, D., Alam, A., Bashir, R. "Selective heating characterization of nanoplate devices for sensing applications", NSTI-Nanotech Vol. 2, pp. 198-201, 2007.
Elibol, O., Reddy, B., Nair, P. R., Dorvel, B., Butler, F., Bergstrom, D. E., Alam, M. A., and Bashir, R., Lab on Chip, 2009 (in press)
Fritz, J., Cooper, E. B., Gaudet, S., Sorger, P. K., Manalis, S. R., P.N.A.S., 99, 14142 (2002).
Gomez, R., Morrisette, D., Bashir, R., IEEE/ASME Journal of Microelectromechanical Systems, 2005, 14, 829-838.
Giuducci, C., Stagni, C., Fischetti, A., Mastromatteo, U., Benini, L., IEEE Sensors J., 6, 2006.

Hanss, M., Biopolymers, 12, 2151, 1973.

Hashimoto, M., Barany, F., Soper, S. A., Biosensors and Bioelectronics, 2006, 21, 1915-1923.

Hong, J., Yoon, D. S., Park, M., Choi, J., Kim, T. S., Im, G., Kim, S., Pak, Y. E., No, K., Japan. J. of Applied Physics, 43, 5639, 2004.

Hou, C. J., Godin, M., Payer, K., Chakrabarti, R., Manalis, S. R., Lab Chip, 7, 347, 2007.

Jungner, G., Jungner, I., Allgen, L. G., Nature, 63, 849 (1949).

Ke, C., Kelleher, A., Berney, H., Sheehan, M., Mathewson, A., Sensors and Actuators B, 2007, 120, 538-544.

Khandurina, J., McKnight, T. E., Jacobson, C., Waters, L. C., Foote, R. S., and Ramsey, J. M., Anal. Chem., 2000, 72, 2995-3000.

Kulski, J. K., Khinsoe, C., Pryce, T., and Christiansen, K., Journal of Clinical Microbiology, 1995, 33, 668-674.

Lagally, E. T., Medintz, I., and Mathies, R. A., Anal. Chem., 2001, 73, 565-570.

Lee, S. W., Bashir, R., Appl. Phys. Lett. 83, 3833, 2003.

Lee, S. W., Yamamoto, T., Fujii, T., The 13th International Conference on Solid-State Sensors, Actuators and Microsystems, 2005.

Li, H., Zheng, Y., Akin, D., Bashir, R., IEEE/ASME Journal of Microelectromechanical Systems. Vol. 14, No. 1, February 2005, pp. 105-111

Liao, C., Lee, G., Wu, J., Chang, C., Hsieh, T., Huang, F., Luo, C., Biosensors and Bioelectronics, 2005, 20, 1341-1348.

Liu, Y., Banada, P. P., Bhattacharya, S., Bhunia, A. K., and Bashir, R., Applied Physics Letters, 92, 143902, 2008.

Liu, Y., Banada, P. P., Bhattacharya, S., Bhunia, A. K., and Bashir, R., IEEE Sensors Conference, 2008.

Northrup, M. A., Ching, M. T., White, R. M., Wilson, R. T., Proceedings of Transducers '93, 1993, 924-926.

Park, I., Li, Z. and Pisano, A. P. "Selective functionalization of silicon micro/nanowire sensors via localized joule heating". IEEE-NEMS Vol. 2, pp.899-904, 2007.

Reddy, B., Jr., Elibol, O. H., Nair, P. R., Dorvel, B., Butler, F., Bergstrom, D. E., Alam, M. A., and Bashir, R., Lab on Chip, 2009 (In press).

Rodriguez, W. R., Christodoulides, N., Floriano, P. N., Graham, S., Mohanty, S., et al. PLoS Med 2005;2:e182.

Sin, M. L. Y., Constantino, V. U., Gau, V., Haake, W. A., Wong, P. K., 3rd IEEE International Conference on Nano/Micro Engineered and Molecular Systems, 2008. NEMS 2008.

Singh, J., and Ekaputri, M., "PCR Thermal Management in an Integrated Lab on a Chip". Journal of Physics: Conference Series. Vol. 34, pp. 222-227, 2006.

Taylor, T., Winn-Dean, E., Picozza, E., Woudenberg, T., Albin, M., Nucleic Acids Res., 1997, 25, 3164-3168.

Yamamoto, K., Rajagopalan, M., and Madiraju, M., J. Biochem., 2002, 131, 219-224.

Yang, L., Banada, P. P., Chatni, M. R., Lim, K., Ladisch, M., Bhunia, A. K., Bashir, R., Lab Chip, 6, 896-905, 2006.

Yi, M., Jeong, K., Lee, L. P., Biosensors and Bioelectronics, 20, 1320, 2005.

Yoon, D. S., Lee, Y.-S. et al., "Precise Temperature Control and Rapid Thermal Cycling in a Micromachined DNA polymerase Chain Reaction Chip". Journal of Micromechanics and Microengineering, vol. 12, pp. 813-823, 2002.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A chemical sensor device for sensing one or more analytes, the chemical sensor device comprising:
   a semiconductor field effect sensor comprising a source, a drain, a gate and a sensing region, wherein the sensing region comprises a nanowire or a nanoplate positioned between the source and drain and the gate is positioned at least partially below the sensing region, the source, and the drain, wherein the sensing region is a temperature controllable sensing region;
   an electrostatic lens electrode positioned over the semiconductor field effect sensor, wherein the electrostatic lens electrode includes a first opening above the sensing region for passing the one or more analytes to be sensed to the sensing region;
   a first passivation layer positioned between the electrostatic lens electrode and the source and the drain of the semiconductor field effect sensor for electrically isolating the electrostatic lens electrode from the source and for electrically isolating the electrostatic lens electrode from the drain; and
   an AC voltage controller electrically connected to the gate and both the source and the drain for providing a preselected AC voltage between the gate and the source and between the gate and the drain;
   wherein application of an AC voltage between the gate and the source and between the gate and the drain causes localized dielectric heating of the sensing region, thereby providing for temperature control of the temperature controllable sensing region.

2. The chemical sensor device of claim 1, further comprising a DC voltage controller electrically connected to the electrostatic lens electrode and the gate for providing a preselected DC voltage between the electrostatic lens electrode and the gate.

3. The chemical sensor device of claim 1, wherein the first opening has a cross-sectional dimension selected from 0.01 to 50 µm.

4. The chemical sensor device of claim 1, wherein a distance between the electrostatic lens electrode and the semiconductor field effect sensor is selected from 0.01 to 5 µm.

5. The chemical sensor device of claim 1, further comprising one or more probe molecules immobilized on the surface of the sensing region.

6. The chemical sensor device of claim 1, wherein the first passivation layer includes a second opening above the sensing region for passing the one or more analytes to be sensed to the sensing region.

7. The chemical sensor device of claim 6, wherein the second opening has a cross-sectional dimension selected from 0.01 to 50 µm.

8. The chemical sensor device of claim 1, wherein the first passivation layer is at least partially disposed on the sensing region for immobilizing one or more probe molecules above the sensing region.

9. The chemical sensor device of claim 1, further comprising a probe molecule immobilized on a surface of the first passivation layer.

10. The chemical sensor device of claim 1, wherein the first passivation layer includes oxygen.

11. The chemical sensor device of claim 1, wherein at least a portion of the first passivation layer has a composition having a stoichiometry of $MO_x$, wherein M is a semiconductor and x is selected from the range of 0-2.

12. The chemical sensor device of claim 1, wherein the first passivation layer comprises nitrogen.

13. The chemical sensor device of claim 1, wherein at least a portion of the first passivation layer has a composition having a stoichiometry of $MN_y$, wherein M is a semiconductor and y is selected from the range of 0-1.34.

14. The chemical sensor device of claim 1, wherein the first passivation layer comprises silicon.

15. The chemical sensor device of claim 1, wherein the first passivation layer comprises a silicon rich layer, $SiO_2$, $Si_3N_4$, silicon oxynitride, $Al_2O_3$, AlN, $HfO_2$, polyimide, photoresist or a depositable or growable insulator.

16. The chemical sensor device of claim 1, wherein the first passivation layer comprises a layer having a mixture of aluminum and oxygen.

17. The chemical sensor device of claim 1, wherein the first passivation layer has a thickness selected from 0.01 to 5 µm.

18. The chemical sensor device of claim 1, further comprising a second passivation layer located on the electrostatic lens electrode, wherein the second passivation layer includes a third opening above the sensing region for passing the one or more analytes to be sensed to the sensing region.

19. The chemical sensor device of claim 18, wherein the third opening has a cross-sectional dimension selected from 0.1 to 50 µm.

20. The chemical sensor device of claim 18, wherein the second passivation layer comprises a material selected from the group consisting of: $SiO_2$, $Si_3N_4$, silicon oxynitride, $Al_2O_3$, AlN, $HfO_2$, polyimide and photoresist.

21. The chemical sensor device of claim 18, wherein the second passivation layer has a thickness selected from 0.1 to 5 µm.

22. The chemical sensor device of claim 1, wherein the electrostatic lens electrode comprises a material selected from the group consisting of: gold, platinum, aluminum, doped poly-silicon, silicon, titanium, nickel, and chromium.

23. The chemical sensor device of claim 1, wherein the electrostatic lens electrode has a thickness selected from 0.01 to 5 µm.

24. The chemical sensor device of claim 1, wherein the gate comprises a semiconductor substrate.

25. The chemical sensor device of claim 1, wherein the gate comprises an electrical contact under a buried oxide layer.

26. The chemical sensor device of claim 1, wherein the semiconductor field effect sensor comprises a semiconductor selected from the group consisting of: silicon, germanium, carbon, any III-V semiconductor, and any II-VI semiconductor.

27. The chemical sensor device of claim 1, wherein the source and drain each comprise doped semiconductor.

28. The chemical sensor device of claim 27, wherein dopants in the doped semiconductor are selected from the group consisting of phosphorus, nitrogen, arsenic, antimony, carbon, and oxygen.

29. The chemical sensor device of claim 1, further comprising a gate electrode located below the semiconductor field effect sensor.

30. The chemical sensor device of claim 1, wherein the chemical sensor is a pH sensor.

31. The chemical sensor device of claim 1, wherein the chemical sensor is a FIN-FET, a double gate SOI FET, a metal gate FET, an extended gate FET or a strained semiconductor FET.

32. A method for detection of a single target analyte molecule, the method comprising the steps of:
provided the chemical sensor of claim 1, wherein the sensing region is functionalized to detect a target analyte molecule;
providing a solution to the field effect sensor, wherein the solution comprises a plurality of analyte molecules including at least one target analyte molecule;
applying a first potential difference between the electrostatic lens electrode and the gate electrode to attract a target analyte molecule to the sensing region;
monitoring an electric parameter of the field effect sensor to determine when a single target analyte molecule is detected by the field effect sensor; and
applying a second potential difference between the electrostatic lens electrode and the gate electrode to repel additional analyte molecules from the sensing region.

33. The method of claim 32, wherein the electrostatic lens electrode includes an opening above the sensing region for passing the one or more analytes to be sensed to the sensing region.

34. The method of claim 32, wherein the second potential difference is of the opposite sign of the first potential difference.

35. The method of claim 32, wherein the monitoring step occurs prior to the application of the first potential difference.

36. The method of claim 32, wherein the monitoring step occurs prior to, during and after the application of the first potential difference.

37. The method of claim 32, wherein the step of applying the second potential difference occurs immediately after the detection of the target analyte during the monitoring step.

38. The method of claim 32, wherein if a target analyte molecule is detected before the application of the first potential difference, the second potential difference is immediately applied.

39. A method for performing PCR on a single target analyte molecule, the method comprising the steps of:
providing the chemical sensor device of claim 1, wherein the sensing region is functionalized for detection of a target analyte molecule by the field effect sensor;
providing a solution to the field effect sensor, wherein the solution comprises a plurality of analyte molecules including at least one target analyte molecule;
applying a first DC voltage between the electrostatic lens electrode and the gate electrode to attract a target analyte molecule to the sensing region;
monitoring an electric parameter of the field effect sensor to determine when a single target analyte molecule is detected by the field effect sensor;
applying a second DC voltage between the electrostatic lens electrode and the gate electrode to repel additional analyte molecules from the sensing region, wherein the second DC voltage is of the opposite sign of the first DC voltage; and
repeating one or more times the steps of:
applying a first AC voltage between the gate electrode and the source and drain to raise the temperature of the target analyte molecule to a first temperature;
terminating the application of voltage between the gate electrode and the source and drain and allowing the temperature of the target analyte molecule to relax to a second temperature; and
applying a second AC voltage between the gate electrode and the source and drain to raise the temperature of the target analyte molecule to a third temperature.

40. The method of claim 39, wherein the solution further comprises components and reagents necessary for performing PCR on the single target analyte molecule.

41. The method of claim 39, further comprising the step of providing a second solution to the field effect sensor before the repeating steps, wherein the second solution comprises components and reagents necessary for performing PCR on the single target analyte molecule.

42. The method of claim 39, further comprising the step of monitoring an electric parameter of the field effect sensor to determine a quantity increase of the target analyte molecule achieved during the repeating steps.

43. The method of claim 39, further comprising the step of monitoring an electric parameter of the field effect sensor to determine a change in pH achieved during the repeating steps.

44. The method of claim 39, further comprising a step of applying a third AC or DC voltage between the electrostatic lens electrode and the gate electrode after raising the temperature of the target analyte molecule to the third temperature.

45. The method of claim 44, wherein the step of applying a third AC or DC voltage is repeated one or more times.

46. The method of claim 39, further comprising a step of measuring the impedance of the solution, thereby detecting amplification of the target molecule.

47. A method for amplification of a target molecule comprising the steps of:
providing a chemical sensor device of claim 1;
providing a solution containing at least one target molecule to a surface of the chemical sensor device;
providing a preselected AC voltage between the gate and the source and drain to heat the chemical sensor device to a preselected temperature; and
transporting the at least one target molecule across the surface of the chemical sensor device.

48. The method of claim 47, wherein the transporting step includes moving the at least one target molecule through a spatial temperature gradient including the temperatures necessary for performing PCR on the at least one target molecule.

49. The method of claim 48, wherein the spatial temperature gradient includes a denaturation temperature, an extension temperature and an annealing temperature.

50. The method of claim 47, wherein the transporting includes passive transport of the at least one target molecule.

51. The method of claim 50, wherein the passive transport is diffusion of the at least one target molecule.

52. The method of claim 47, wherein the transporting includes active transport of the at least one target molecule.

53. The method of claim 52, wherein the active transport is by dielectrophoresis of the at least one target molecule.

54. The method of claim 47, wherein the transporting is by electro-thermal movement of the at least one target molecule.

55. An array of chemical sensors comprising one or more chemical sensor devices of claim 1.

56. The array of chemical sensors of claim 55, wherein each element of the array is independently electrically addressable.

57. A method for sensing a structure containing nucleic acids, the method comprising the steps of:
providing a chemical sensor device of claim 1;
providing a solution having one or more nucleic acid containing structures to the chemical sensor device; and
monitoring an electrical parameter of the chemical sensor device to detect when a nucleic acid containing structure is loaded into the chemical sensor device.

58. The method of claim 57, wherein the nucleic acid containing structure is selected from the group consisting of cells, mammalian cells, plant cells, bacterial cells, spores and viruses.

59. The method of claim 57, further comprising the step of providing a first DC voltage between the electrostatic lens electrode and the gate electrode of the chemical sensor device element to attract and/or trap the nucleic acid containing structure.

60. The method of claim 59, further comprising the step of providing a second DC voltage between the electrostatic lens electrode and the gate electrode of the chemical sensor device element to repel additional nucleic acid containing structures.

61. The method of claim 57, further comprising the step of heating the nucleic acid containing structure to lyse the structure and release the nucleic acid into the chemical sensor device.

62. The method of claim 61, wherein the heating step comprises providing an AC voltage between the gate electrode and the source and drain of the chemical sensor device.

63. The method of claim 61, wherein heating comprises heating the nucleic acid containing structure to a temperature selected from about 95 and 100° C. for 5 minutes.

64. The method of claim 61, further comprising the step of amplifying the released nucleic acids.

65. The method of claim 64, wherein amplification of the released nucleic acids is achieved by PCR.

66. The method of claim 64, wherein the amplification step includes repeating one or more times the steps of:
   applying a first AC voltage between the gate electrode and the source and drain of the individual chemical sensor device elements to raise the temperature of the fragments to a first temperature;
   terminating the application of voltage between the gate electrode and the source and drain of the individual chemical sensor device elements and allowing the temperature of the fragments to relax to a second temperature; and
   applying a second AC voltage between the gate electrode and the source and drain of the individual chemical sensor device elements to raise the temperature of the fragments to a third temperature.

67. The method of claim 61, further comprising the step of monitoring an electric parameter of the field effect sensor to determine a quantity increase of the released nucleic acids achieved during the repeating steps.

68. The method of claim 61, further comprising the step of monitoring an electric parameter of the field effect sensor to determine a change in pH achieved during the repeating steps.

69. The method of claim 61, further comprising the step of heating the chemical sensor device to bind the released nucleic acids to the sensing region of the chemical sensor device.

70. The method of claim 69, wherein the heating is achieved by applying a first AC voltage between the gate electrode and the source and drain of the chemical sensor device.

71. The method of claim 61, further comprising a step of providing to the chemical sensor device the necessary reagents for the synthesis of the complements to the released nucleic acids.

72. The method of claim 61, further comprising a step of monitoring an electrical parameter to sense a change in the charge present at the sensing region as complements to the released nucleic acids are synthesized.

73. The method of claim 61, further comprising a step of monitoring an electrical parameter to sense a change in the pH as complements to the plurality of fragments are synthesized.

74. The chemical sensor of claim 1, wherein the temperature controllable sensing region includes a nucleic acid denaturation temperature range, a nucleic acid extension temperature range and a denatured and extended nucleic acid annealing temperature range, and wherein:
   the nucleic acid denaturation temperature range is from 90° C. to 100° C.;
   the nucleic acid extension temperature range is from 68° C. to 75° C.; and
   the denatured and extended nucleic acid annealing temperature range is from 68° C. to 75° C.

75. The chemical sensor of claim 1, wherein the temperature controllable sensing region comprises a thermal gradient in the sensing region.

76. The chemical sensor of claim 75, wherein the thermal gradient has a local temperature minimum in a center position of the sensing region.

77. The chemical sensor of claim 1, wherein the temperature controllable sensing region comprises a time varying temperature profile having a nucleic acid denaturation temperature, extension temperature, and an annealing temperature at non-overlapping time points.

78. The chemical sensor of claim 1, wherein the first passivation layer is a continuous layer that separates the semiconductor field effect transistor from the electrostatic lens electrode and that covers the sensing region, wherein the first passivation layer has a reduced thickness over the sensing region that is less than a thickness of the first passivation layer between the field effect transistor and the electrostatic lens electrode.

79. The chemical sensor of claim 78, wherein the reduced thickness of the first passivation layer that covers the sensing region is selected from 0.001 μm and 0.1 μm.

80. The chemical sensor of claim 2, wherein the DC voltage controller has reversible polarity to attract an analyte at a first potential difference and to repel an analyte at a second potential difference having a polarity that is opposite to a polarity of the first potential difference.

* * * * *